(12) United States Patent
Christie et al.

(10) Patent No.: US 10,518,076 B2
(45) Date of Patent: Dec. 31, 2019

(54) FLUID LINE LOCKING DEVICE

(71) Applicants: Alexander L. Christie, Pittsburgh, PA (US); Kimberly P. Daloise, Natrona Heights, PA (US); Samuel K. Luketich, Scenery Hill, PA (US); Drake D. Pedersen, Mt. Pleasant, SC (US); Hannah Joy Houck, Grove City, PA (US)

(72) Inventors: Alexander L. Christie, Pittsburgh, PA (US); Kimberly P. Daloise, Natrona Heights, PA (US); Samuel K. Luketich, Scenery Hill, PA (US); Drake D. Pedersen, Mt. Pleasant, SC (US); Hannah Joy Houck, Grove City, PA (US)

(73) Assignee: Alexander L. Christie, Pittsburgh, PA (US)

( * ) Notice: Subject to any disclaimer, the term of this patent is extended or adjusted under 35 U.S.C. 154(b) by 260 days.

(21) Appl. No.: 15/355,467

(22) Filed: Nov. 18, 2016

(65) Prior Publication Data

US 2017/0157384 A1    Jun. 8, 2017

Related U.S. Application Data

(60) Provisional application No. 62/263,150, filed on Dec. 4, 2015.

(51) Int. Cl.
*A61M 39/10* (2006.01)

(52) U.S. Cl.
CPC . *A61M 39/1011* (2013.01); *A61M 2039/1033* (2013.01); *A61M 2039/1066* (2013.01)

(58) Field of Classification Search
CPC ...... A61M 39/1011; A61M 2039/1066; A61M 2039/1033
USPC ............................................. 285/80, 114, 419
See application file for complete search history.

(56) References Cited

U.S. PATENT DOCUMENTS

| | | | | |
|---|---|---|---|---|
| 3,711,632 A * | 1/1973 | Ghirardi | ................... | H02G 3/06 285/419 |
| 3,982,779 A * | 9/1976 | Hickey | ................... | F16L 21/06 285/328 |
| 4,043,333 A * | 8/1977 | Munsch | ................ | A61M 39/04 138/103 |
| 4,340,052 A * | 7/1982 | Dennehey | .......... | A61M 39/1011 604/317 |
| 4,405,312 A * | 9/1983 | Gross | ................. | A61M 39/1011 604/29 |
| 4,432,759 A * | 2/1984 | Gross | ................. | A61M 39/1011 285/419 |
| 4,432,767 A * | 2/1984 | Lobdell | ................. | A61M 39/04 604/86 |
| 4,473,369 A * | 9/1984 | Lueders | ............. | A61M 39/1011 285/419 |
| 4,596,571 A * | 6/1986 | Bellotti | ............. | A61M 39/1011 604/411 |
| 4,631,056 A * | 12/1986 | Dye | ................... | A61M 39/1011 285/3 |

(Continued)

*Primary Examiner* — David Bochna

(57) ABSTRACT

A fluid line locking device has two enclosing components connected through a hinge and rotatable from a closed configuration to an open configuration. The fluid line locking device also has a lock configured to secure the two enclosing components in the closed configuration.

19 Claims, 32 Drawing Sheets

(56) References Cited

U.S. PATENT DOCUMENTS

| | | | | |
|---|---|---|---|---|
| 5,347,084 A * | 9/1994 | Roney | ............... | G02B 6/4447 |
| | | | | 174/92 |
| 5,531,695 A * | 7/1996 | Swisher | ............ | A61M 39/1011 |
| | | | | 604/533 |
| 5,647,612 A * | 7/1997 | Yoshida | ............... | F16L 21/06 |
| | | | | 285/13 |
| 5,853,200 A * | 12/1998 | Zieres | ................ | F16L 35/00 |
| | | | | 285/419 |
| 6,217,564 B1 * | 4/2001 | Peters | ............ | A61M 39/1011 |
| | | | | 604/111 |
| 6,311,734 B1 * | 11/2001 | Petrovic | ............... | B05B 15/65 |
| | | | | 285/45 |
| 6,832,791 B2 * | 12/2004 | Legeai | ............... | F16L 21/065 |
| | | | | 285/421 |
| 6,881,901 B2 * | 4/2005 | Egan | ............... | H02G 15/013 |
| | | | | 16/2.1 |
| 7,014,225 B1 * | 3/2006 | Goodsel | ............... | F16L 23/04 |
| | | | | 285/363 |
| 7,240,930 B2 * | 7/2007 | Stravitz | ............... | D06F 58/20 |
| | | | | 285/419 |
| 7,758,082 B2 | 7/2010 | Weigel et al. | | |
| 7,780,794 B2 | 8/2010 | Rogers et al. | | |
| 7,798,837 B1 * | 9/2010 | Gardner | ............ | G01G 23/017 |
| | | | | 174/66 |
| 7,857,805 B2 | 12/2010 | Raines | | |
| 8,063,306 B2 * | 11/2011 | Zhong | ............... | H02G 15/113 |
| | | | | 174/92 |
| 8,181,999 B2 * | 5/2012 | Cromarty | ............ | F16L 25/0018 |
| | | | | 285/419 |
| 8,262,308 B2 * | 9/2012 | Peng | ............... | F16B 5/0635 |
| | | | | 285/419 |
| 9,404,258 B2 * | 8/2016 | Yun | ............... | E04C 5/165 |
| 9,742,171 B2 * | 8/2017 | Nooner | ............... | H01R 13/5213 |
| 9,926,900 B2 * | 3/2018 | Sasinowski | .......... | F02M 55/004 |
| 2010/0210990 A1 * | 8/2010 | Lyons | ............... | A61M 39/1011 |
| | | | | 604/6.16 |
| 2013/0081849 A1 * | 4/2013 | Simmons | ............ | H01R 9/223 |
| | | | | 174/50.5 |

* cited by examiner

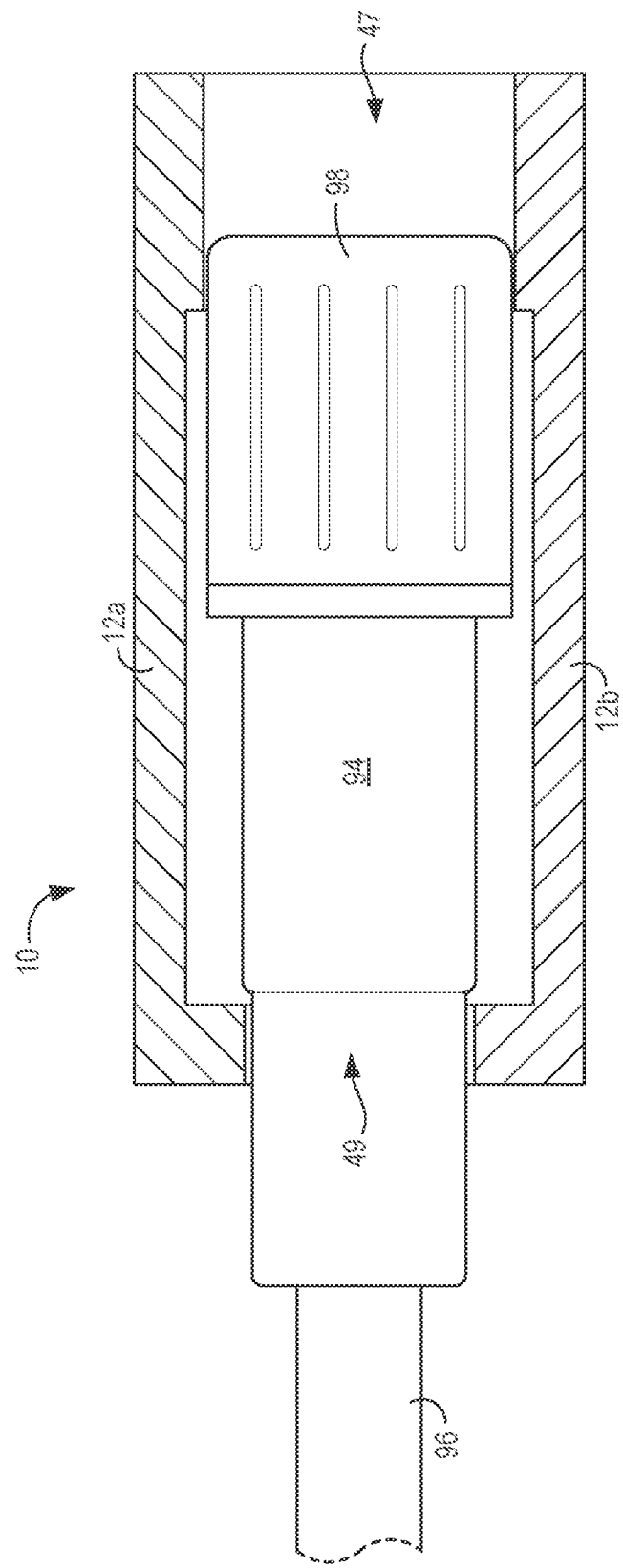

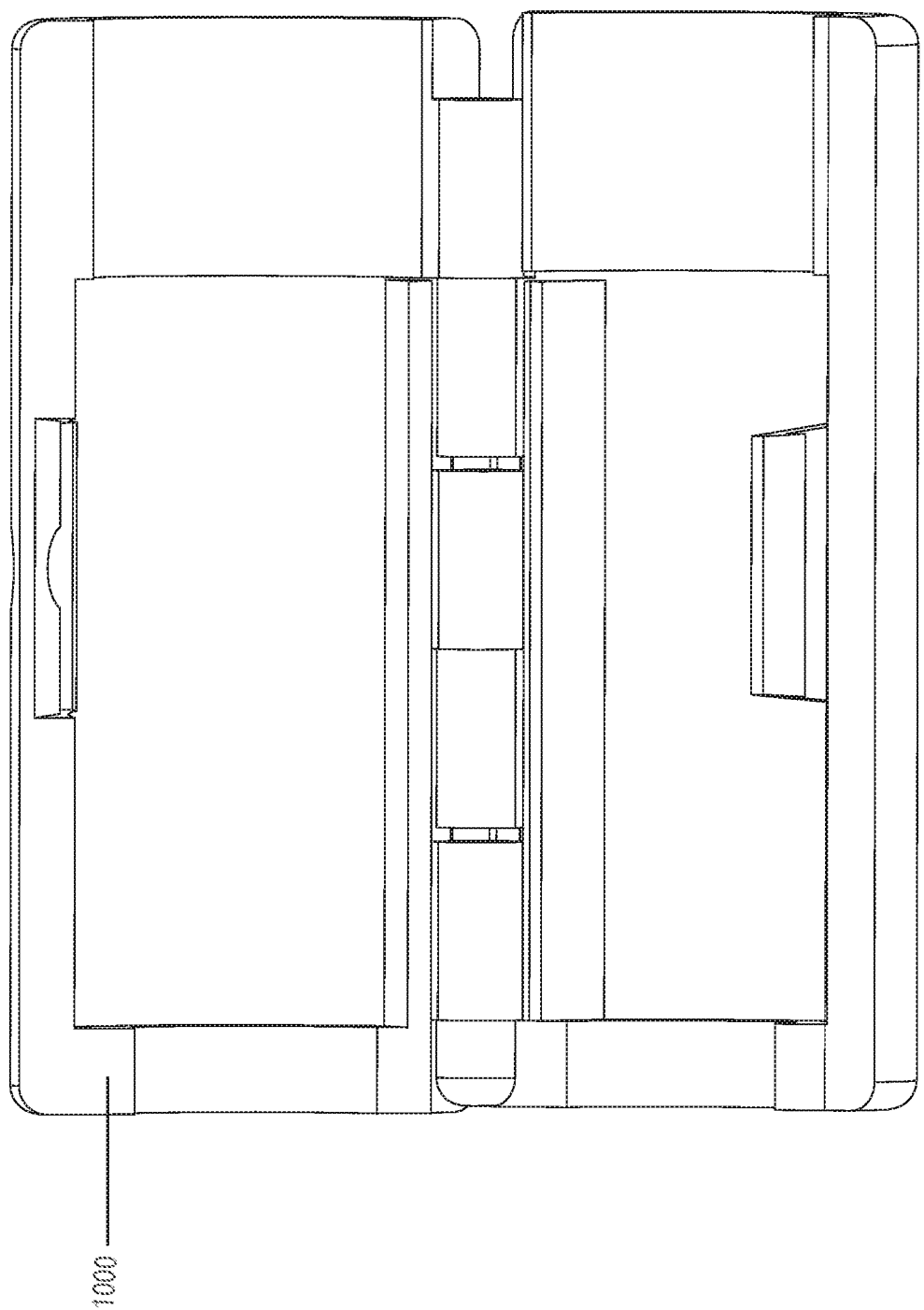

FLUID LINE LOCKING DEVICE

BACKGROUND

The information described in this background section is not admitted to be prior art.

A central venous catheter (CVC), also known as a central line, is a catheter placed into a large vein of a medical patient, for example, into the internal jugular vein in a patient's neck, the subclavian vein or axillary vein in a patient's chest, the femoral vein in a patient's groin, or into a vein in a patient's arm (e.g., the cephalic vein, basilic vein, or brachial vein) (i.e., a peripherally inserted central catheter (PICC line)). Central lines can be used to administer medications, fluids, and/or parenteral nutrition to patients, to obtain blood specimens for testing, and to measure central venous blood pressure. Central lines also can be used for patient dialysis.

Central lines and other types of catheters generally employ standard Luer lock fittings that provide a disconnectable/reconnectable fluid connection between the tubing of the catheter line and the tubing of an IV source or other line. Central lines and other types of catheters, particularly through the Luer lock connections, provide pathways for bacteria to enter into the bloodstream, which can lead to sepsis or other infections. For example, tens of thousands of central line-associated bloodstream infections (CLABSIs) occur in medical patients every year, contributing to thousands of patient deaths, and substantially increasing the costs of medical care. CLABSIs and other catheter-associated infections are particularly problematic in pediatric patients, who have a substantially higher tendency to disconnect the Luer fittings on their central lines or other catheters, thereby separating the catheter lines from IV or other source lines, exposing the catheter line to the environment, and compromising the sterility of the line.

SUMMARY

This specification relates to fluid line locking devices. More particularly, this specification relates to fluid line locking devices configured to enclose and secure fluid line connection joints from disconnection. Even more particularly, this specification relates to fluid line locking devices configured to enclose and secure Luer lock connections from disconnection.

In one example, a fluid line locking device comprises a first enclosing component and a second enclosing component connected to the first enclosing component through a hinge. The first enclosing component and the second enclosing component are rotatable around the hinge from a closed configuration to an open configuration. The fluid line locking device further comprises a lock configured to secure the first enclosing component and the second enclosing component in the closed configuration.

In another example, a fluid line locking device comprises a first enclosing component and a second enclosing component connected to the first enclosing component through a hinge. The first enclosing component and the second enclosing component are rotatable around the hinge from a closed configuration to an open configuration. The fluid line locking device further comprises a lock configured to secure the first enclosing component and the second enclosing component in the closed configuration. The lock comprises a first lock flange located on an interior surface of the first enclosing component, a self-locking arm located on an interior surface of the second enclosing component, a second lock flange located on the self-locking arm, and a lock actuation aperture extending from an exterior surface of the first enclosing component and through the first lock flange.

In another example, a fluid line locking device comprises a first hemi-cylindrical enclosing component and a second hemi-cylindrical enclosing component connected to the first enclosing component through a living hinge. The living hinge is integrally connected to the first enclosing component and the second enclosing component, and the first enclosing component and the second enclosing component are rotatable around the living hinge from a closed configuration to an open configuration. The fluid line locking device further comprises a lock configured to secure the first hemi-cylindrical enclosing component and the second hemi-cylindrical enclosing component in the closed configuration. The lock comprises a first lock flange integrally formed in an interior surface of the first hemi-cylindrical enclosing component, a self-locking arm integrally formed on an interior surface of the second hemi-cylindrical enclosing component, a second lock flange integrally formed on the self-locking arm, and a lock actuation aperture extending from an exterior surface of the first hemi-cylindrical enclosing component and through the first lock flange. The fluid line locking device further comprises a first proximal bearing surface and a first distal bearing surface located at opposite longitudinal ends of the first hemi-cylindrical enclosing component and separated by a first interior surface of the first hemi-cylindrical enclosing component. The fluid line locking device further comprises a second proximal bearing surface and a second distal bearing surface located at opposite longitudinal ends of the second hemi-cylindrical enclosing component and separated by a second interior surface of the second hemi-cylindrical enclosing component. The first proximal bearing surface and the second proximal bearing surface collectively form a proximal end aperture in the fluid line locking device in the closed configuration. The first distal bearing surface and the second distal bearing surface collectively form a distal end aperture in the fluid line locking device in the closed configuration. The first proximal bearing surface and the second proximal bearing surface are structured and dimensioned to secure a standard male Luer lock fitting within an interior volume of the fluid line locking device in the closed configuration. The first distal bearing surface and the second distal bearing surface are structured and dimensioned to secure a standard female Luer lock fitting within the interior volume of the fluid line locking device in the closed configuration.

It is understood that the inventions described in this specification are not necessarily limited to the examples summarized in this Summary.

BRIEF DESCRIPTION OF THE DRAWINGS

Various features and characteristics of the inventions described in this specification may be better understood by reference to the accompanying figures, in which:

FIG. 7C is schematic partial cross-sectional side view of the fluid line locking device shown in FIGS. 1A-1F engaging and enclosing a female Luer lock fitting and an attached disinfectant cap.

FIG. 12 is a photograph of a prototype fluid line locking device made in accordance with the embodiments shown in FIGS. 1A-4B.

Figure 1A:
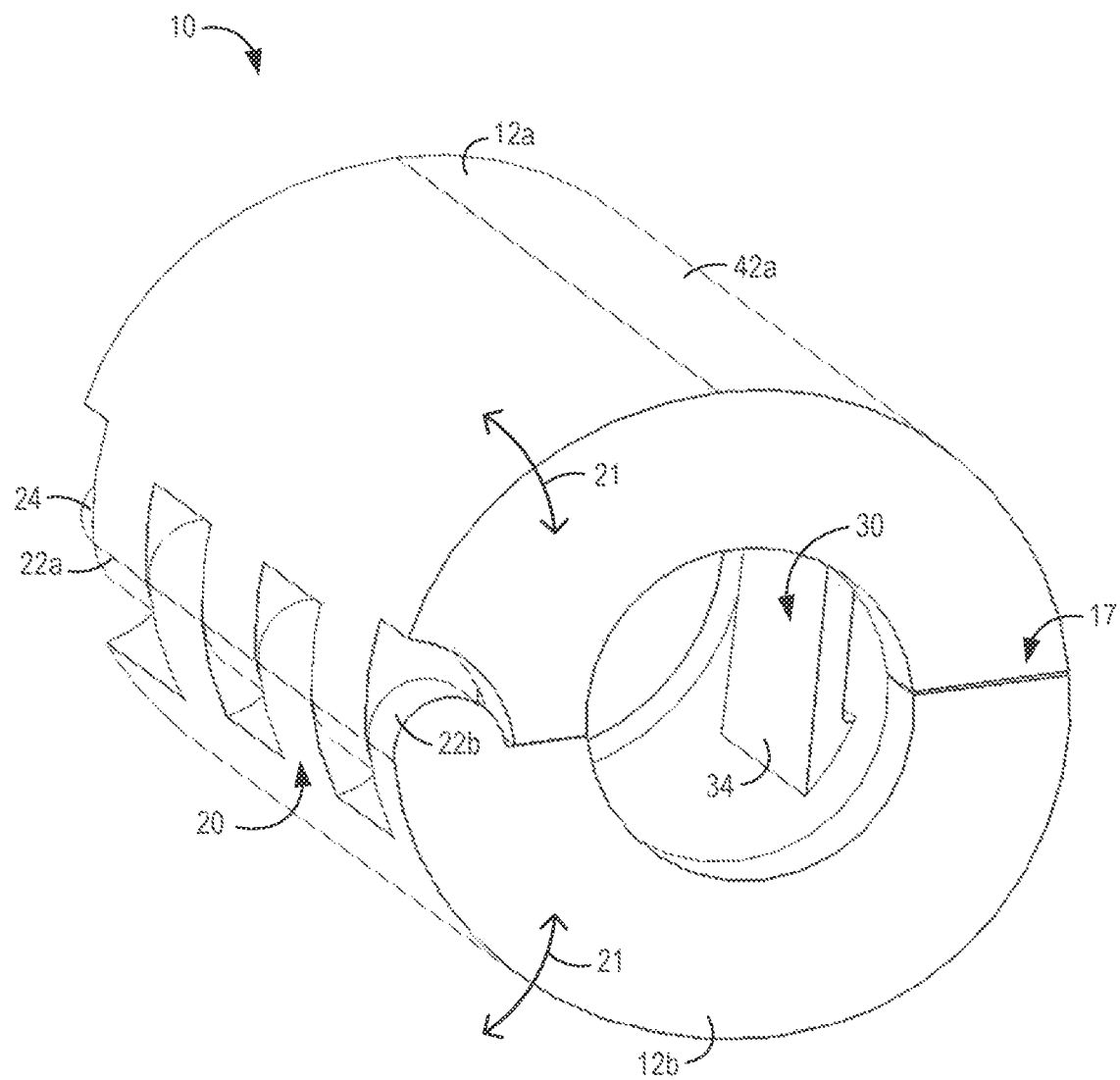
FIGS. 1A and 1B are end perspective views of a fluid line locking device.
Figure 1B:
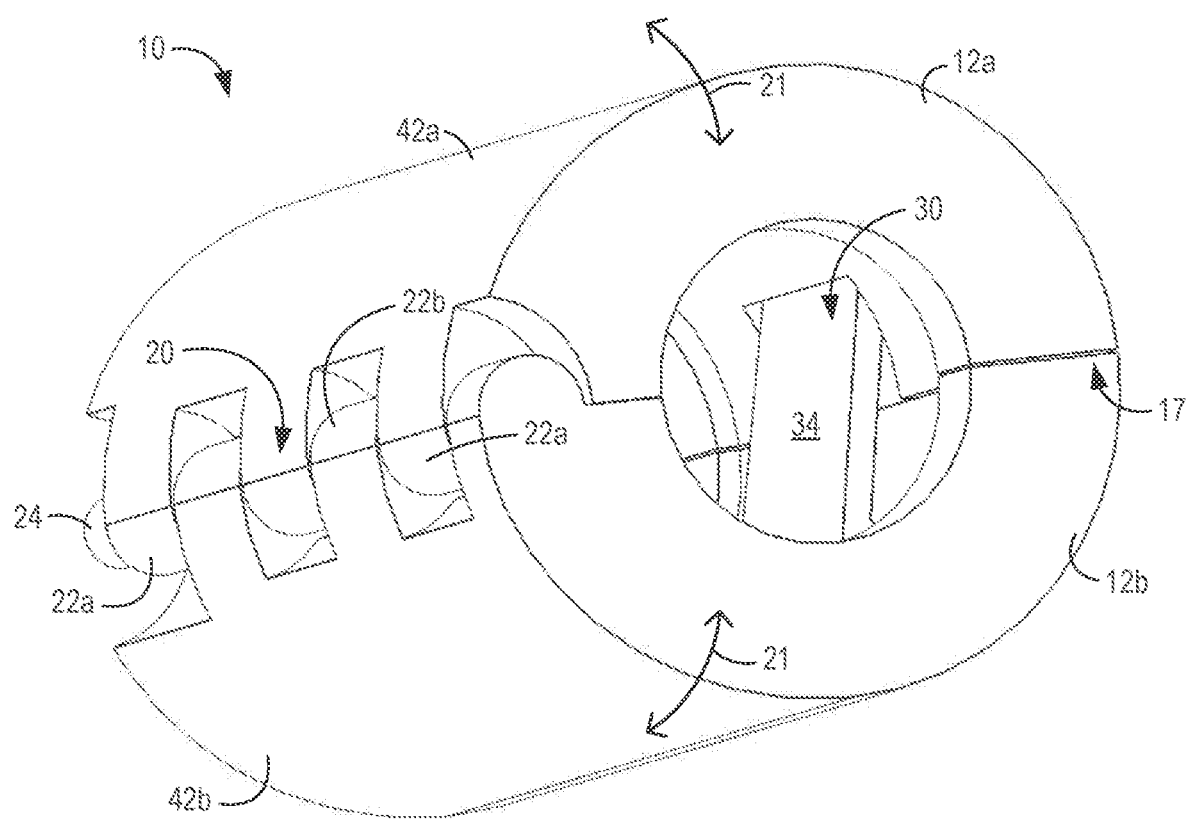
Figure 1C:
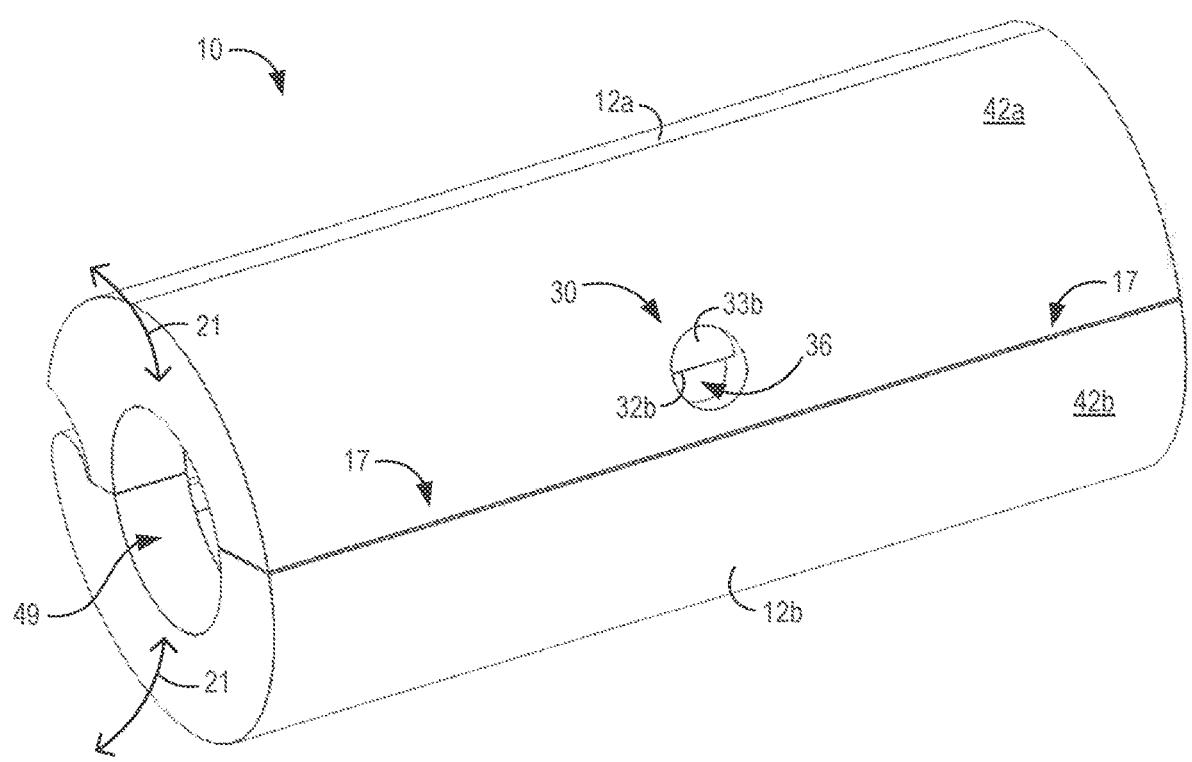
FIG. 1C is a side perspective view of the fluid line locking device shown in FIGS. 1A and 1B, FIGS. 1D and 1E are cross-sectional side perspective views of the fluid line locking device shown in FIGS. 1A-1C.
Figure 1D:
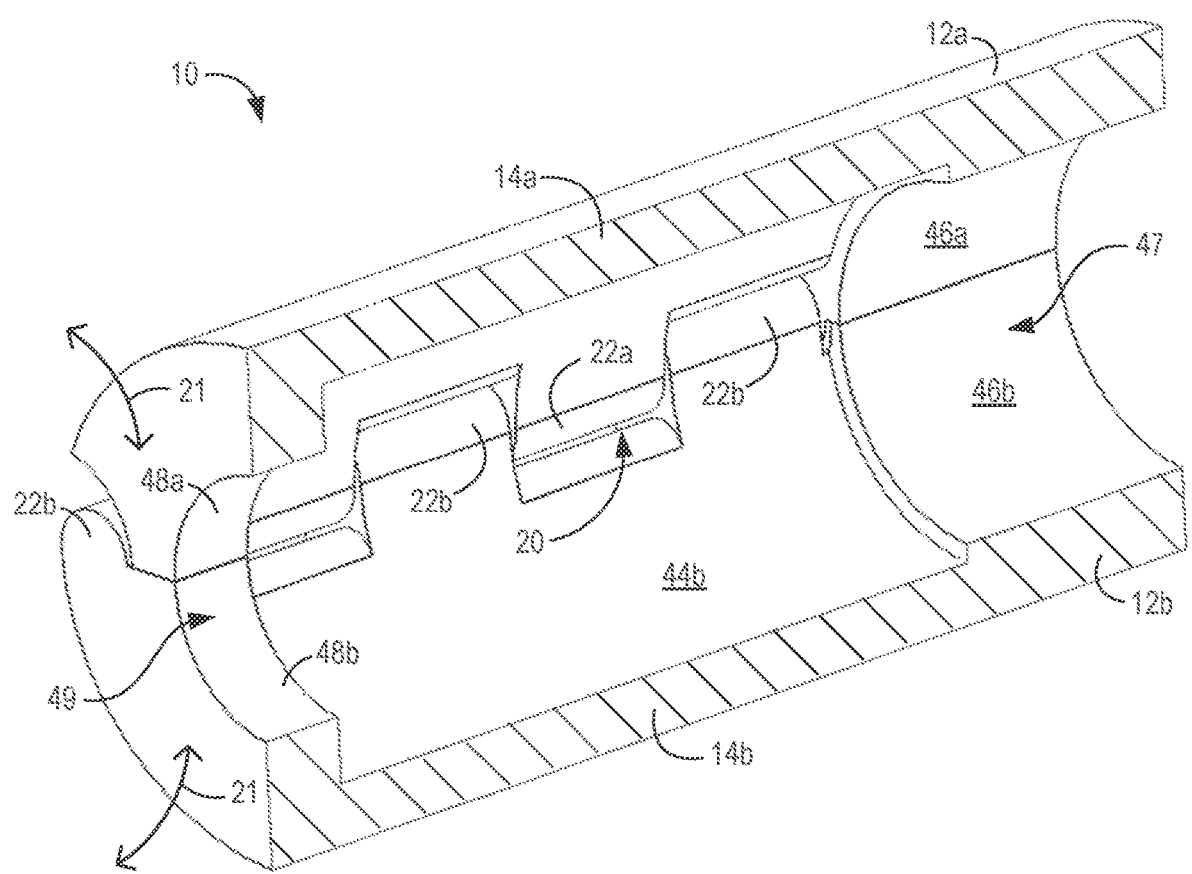
FIG. 1F is an end cross-sectional view of the fluid line locking device shown in FIGS. 1A-1E.
Figure 1E:
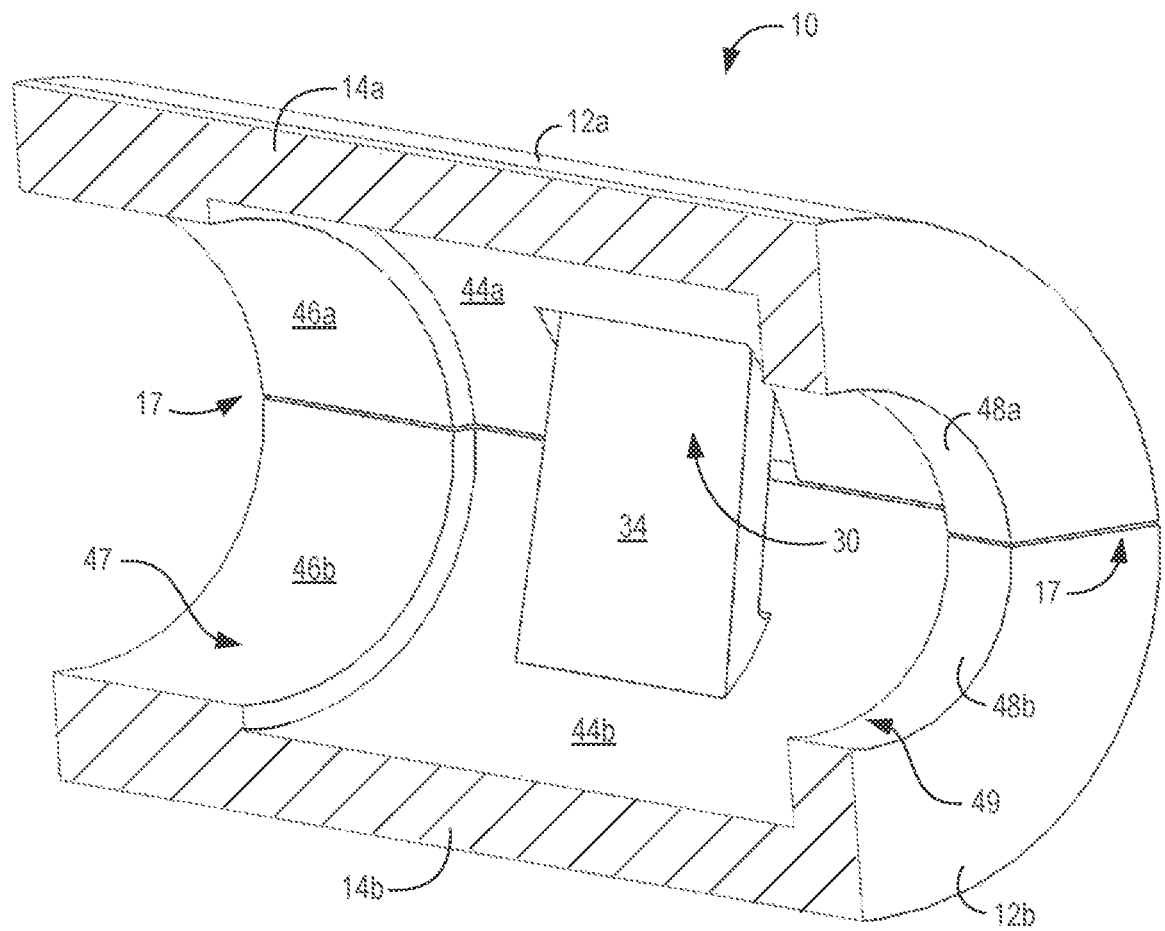

The reader will appreciate the foregoing features and characteristics, as well as others, upon considering the following detailed description of the inventions according to this specification.

DESCRIPTION

As described above, the unintentional disconnection of Luer lock connections in central lines or catheter lines can be problematic in medical environments, particularly with pediatric patients. Additionally, the accidental or otherwise unplanned disconnection of fluid lines, including but not necessarily limited to Luer lock connections, in other environments such as laboratories or industrial locations, can result in undesirable consequences. Accordingly, a fluid line locking device configured to enclose and secure a fluid line connection joint (such as a Luer lock connection, for example) from disconnection would be advantageous.

Referring to FIGS. 1A-4B, a fluid line locking device 10 comprises a first enclosing component 12a and a second, enclosing component 12b. The first enclosing component 12a comprises a first enclosing wall 14a, and the second enclosing component 12b comprises a second enclosing wall 14b. The first enclosing component 12a and the second enclosing component 12b are connected to each other through a hinge 20. The first enclosing component 12a and the second enclosing component 12b are hemi-cylindrical enclosing components that together form the fluid line locking device 10 comprising a cylindrical exterior structure with the hinge 20 located along the length dimension of the cylinder. The longitudinal location of the hinge 20 allows the fluid line locking device 10 to open and close in a "clamshell" manner, as illustrated by arrows 21, wherein the first enclosing component 12a and the second enclosing component 12b rotate around the pin 24 of the hinge 20.

Although the embodiments shown in FIGS. 1A-4B comprise an exterior cylindrical structure, it is nevertheless understood that the first exterior surface 42a of the first enclosing component 12a, and the second exterior surface 42b of the second enclosing component 12b, can independently comprise any shapes or contours. For example, instead of the cylindrical exterior structure, the fluid line locking device 10 can comprise a hexagonal cross-section, an octagonal cross-section, or any other cross-sectional shape perpendicular to the longitudinal axis of the device.

The hinge 20 of the fluid line locking device 10 comprises a butt-mortise hinge wherein intermeshing knuckles 22a and 22b form the barrel of the hinge, and the pin 24 is located within the barrel and through the intermeshed knuckles 22a and 22b. The first knuckles 22a are integrally formed in the first enclosing wall 14a of the first enclosing component 12a, and are mortised flush with the first exterior surface 42a of the first enclosing component 12a. The first knuckles 22a are also mortised flush with the first interior surface 44a of the first enclosing component 12a. The second knuckles 22b are integrally formed in the second enclosing wall 14b of the second enclosing component 12b, and are mortised flush with the second exterior surface 42b of the second enclosing component 12b. The second knuckles 22b are also mortised flush with the second interior surface 44b of the second enclosing component 12b.

The fluid line locking device 10 comprises a lock 30 that secures the first enclosing component 12a and the second enclosing component 12b in the closed configuration shown in FIGS. 1A-1F. The lock 30 comprises a first lock flange 32a formed in the first interior surface 44a of the first enclosing component 12a. The first lock flange 32a is located adjacent to a first oblique guiding surface 33a. The lock 30 also comprises a second lock flange 32b located on a self-locking arm 34. The self-locking arm 34 is located on the second interior surface of 44b of the second enclosing component 12b. The self-locking arm 34 is integrally formed with the second enclosing wall 14b of the second enclosing component 12b. The second lock flange 32b is located on the self-locking arm 34 adjacent to a second oblique guiding surface 33b. The lock 30 also comprises a lock actuation aperture 36 extending from the first exterior surface 42a of the first enclosing component 12a, through the first enclosing wall 14a, through the first lock flange 32a formed in the first interior surface 44a (see FIG. 2A), and to the interior volume of the fluid line locking device 10.

Figure 1F:
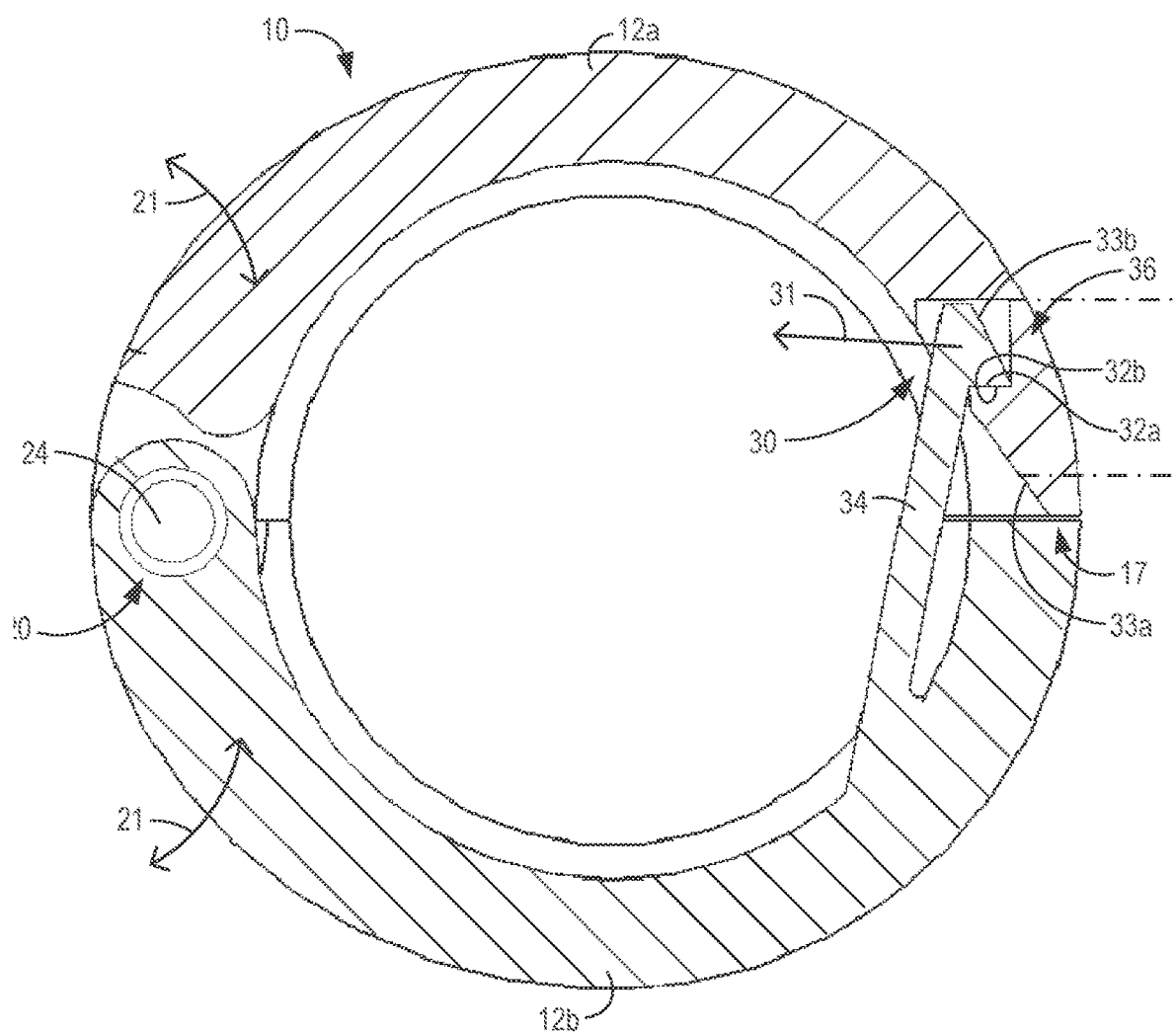
Figure 2A:
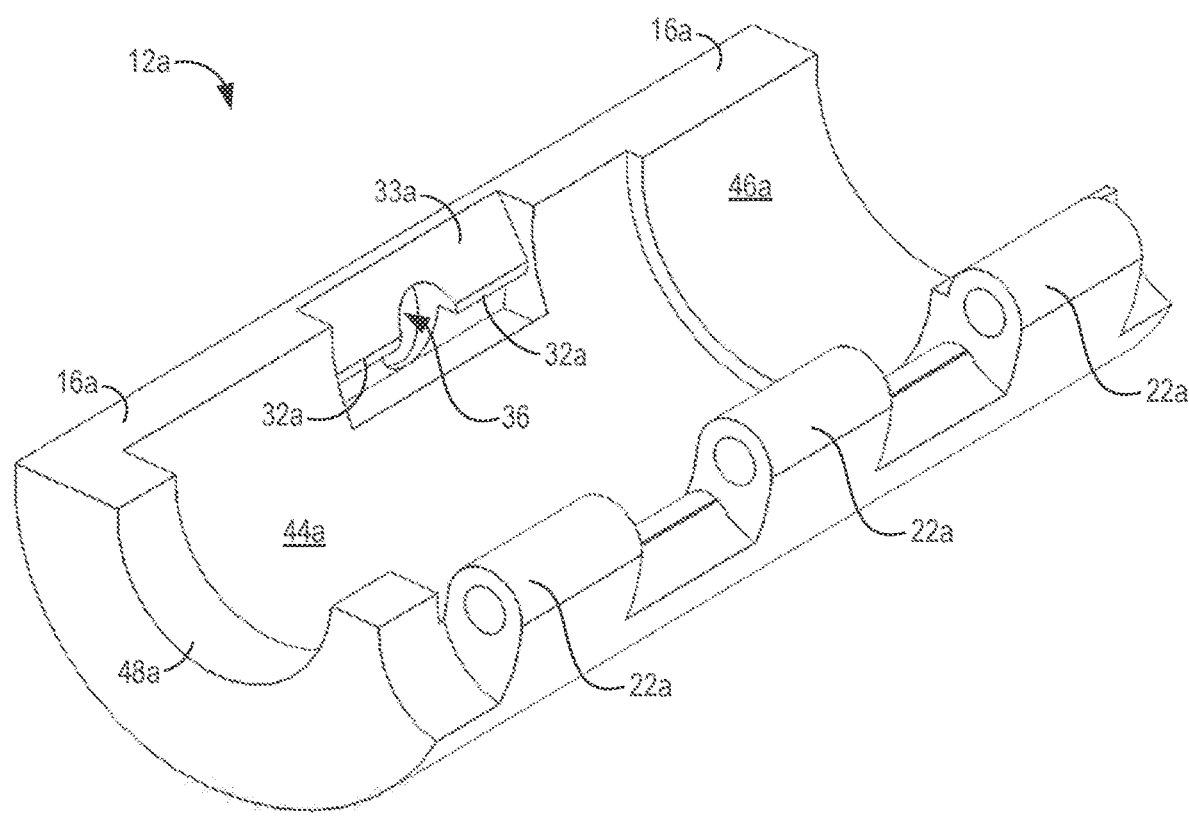
FIGS. 2A and 2B are side perspective views of a first enclosing component of the fluid line locking device shown in FIGS. 1A-1F.
Figure 2B:
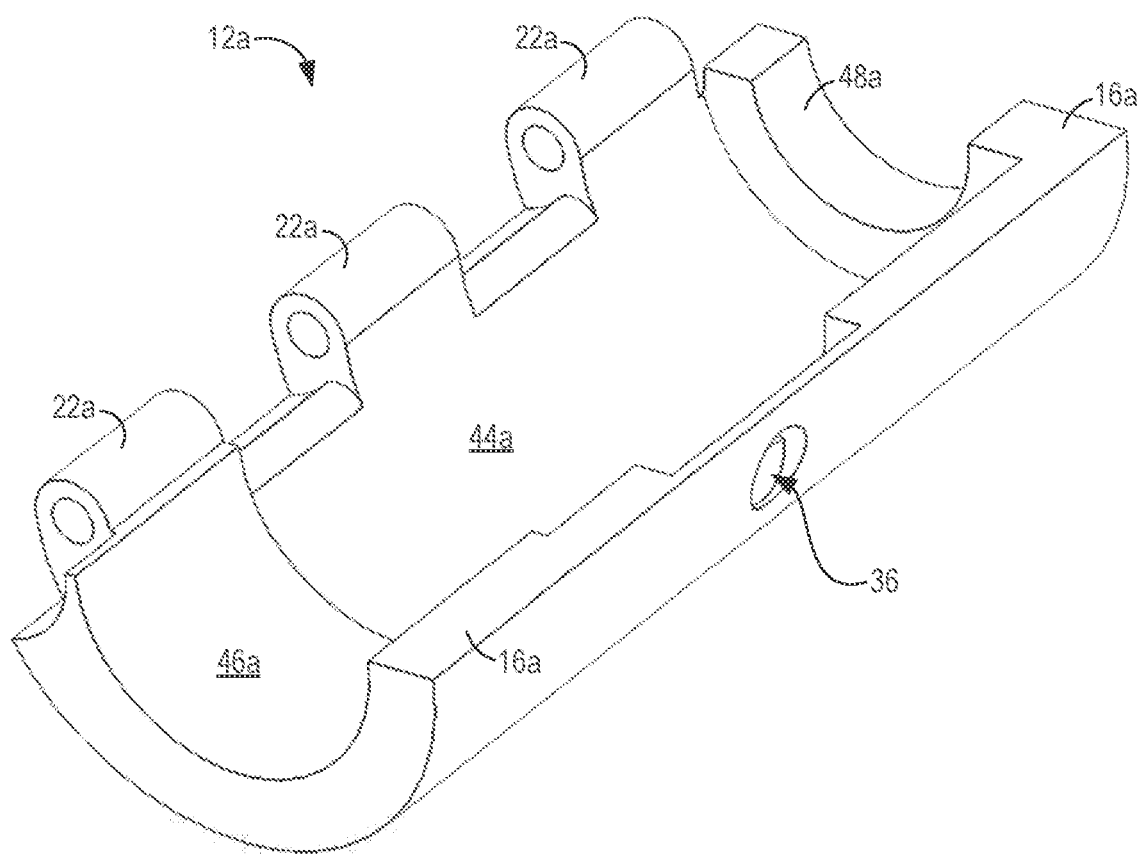
Figure 3A:
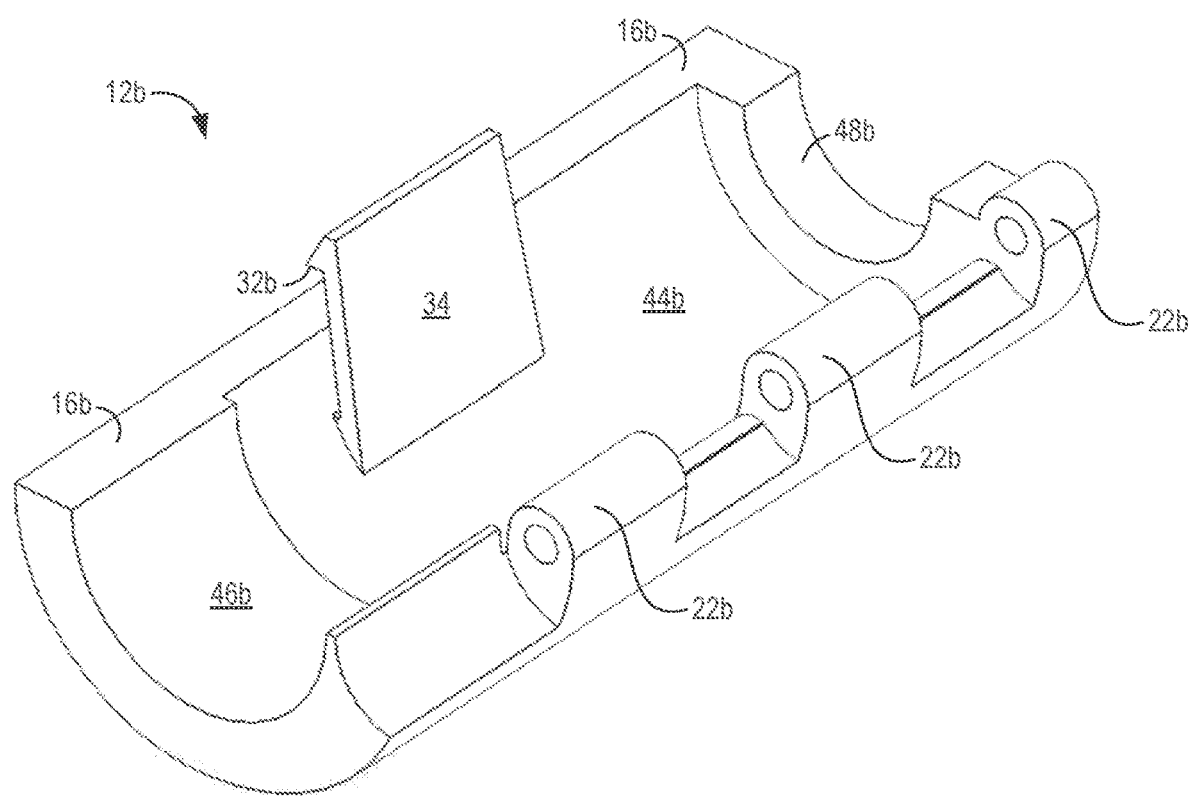
FIGS. 3A and 3B are side perspective views of a second enclosing component of the fluid line locking device shown in FIGS. 1A-1F.
Figure 3B:
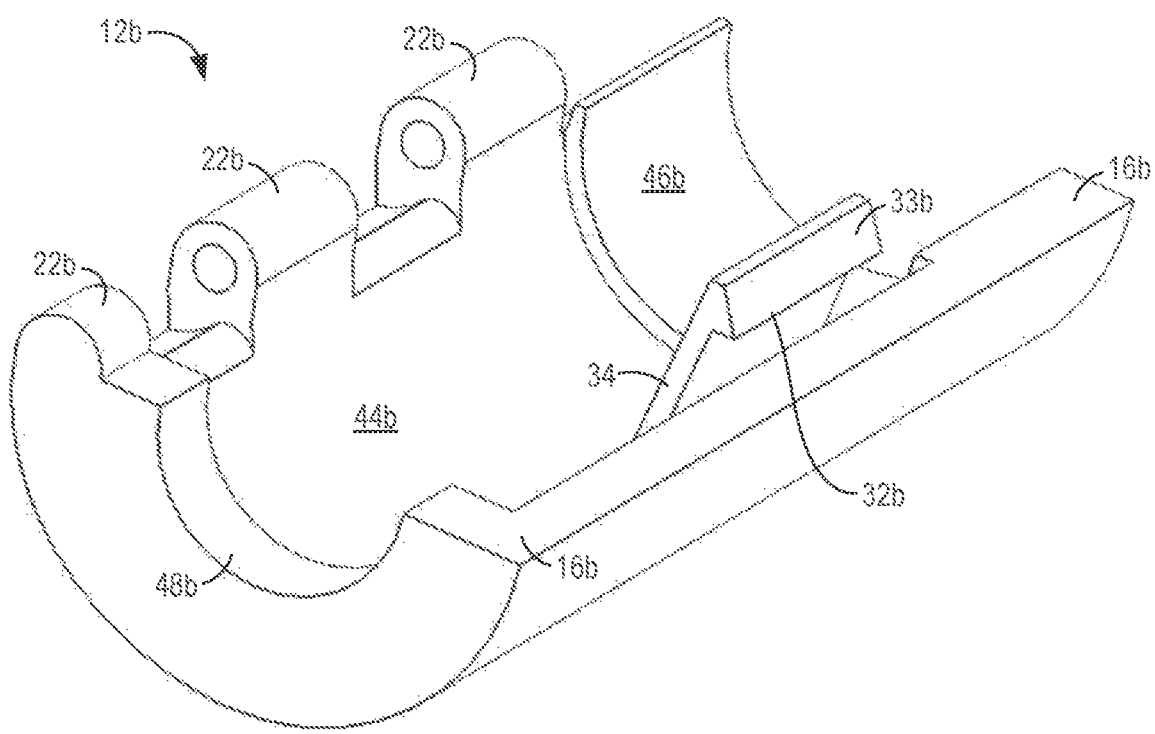
Figure 4A:
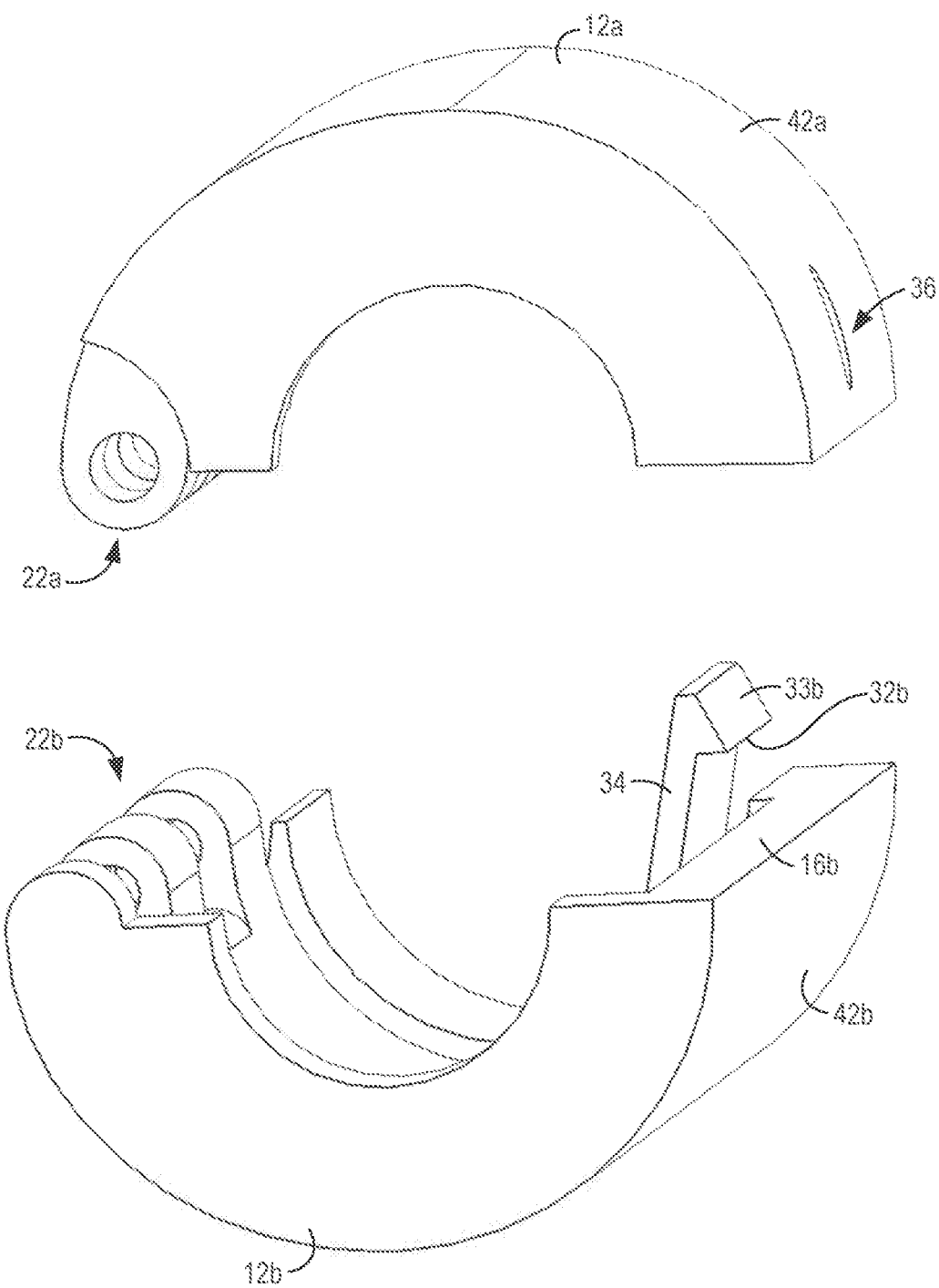
FIG. 4A is an exploded end perspective view of the first enclosing component and the second enclosing component of the fluid line locking device shown in FIGS. 1A-1F.
Figure 4B:
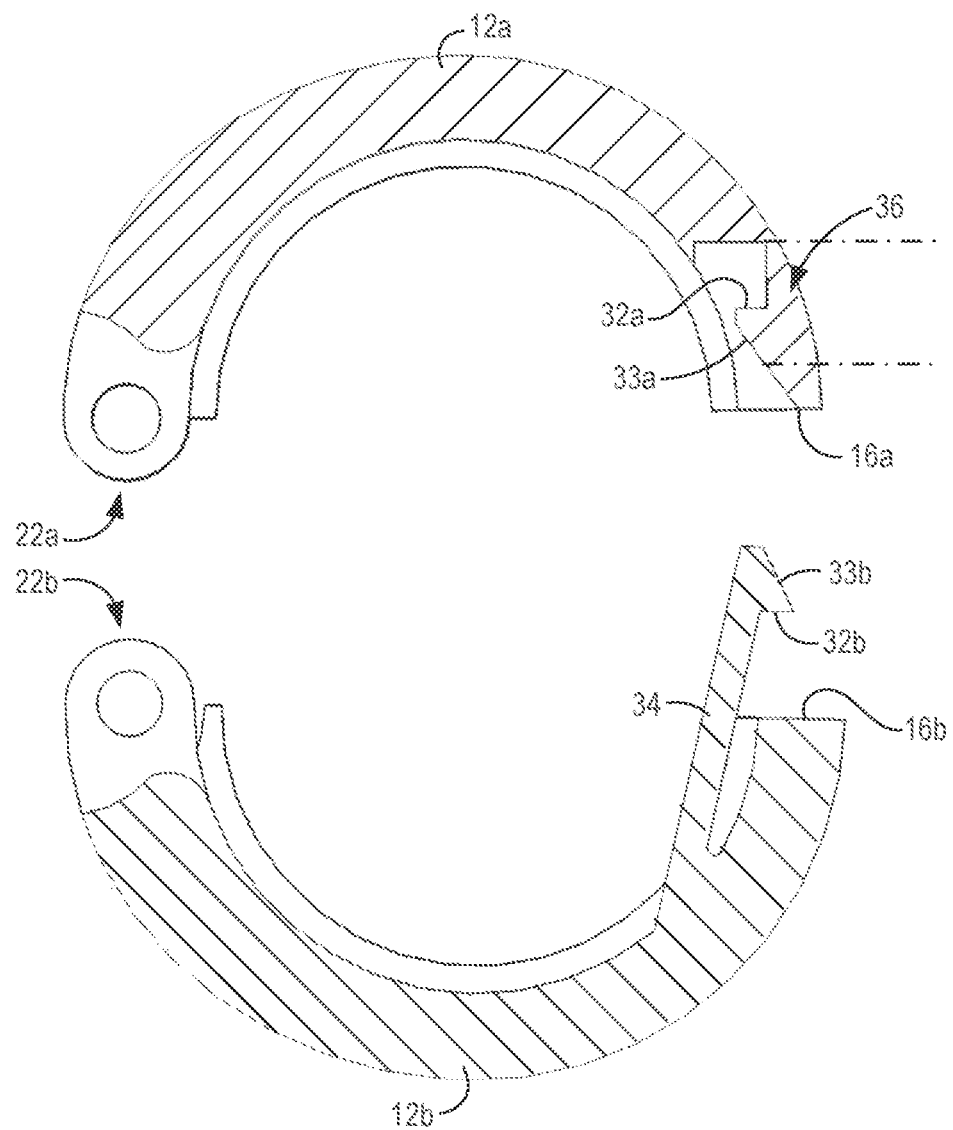
FIG. 4B is an exploded end cross-sectional view of the first enclosing component and the second enclosing component of the fluid line locking device shown in FIGS. 1A-1F.

Referring to FIG. 1F, in operation, the fluid line locking device 10 is in a closed configuration, as shown, and encloses and secures a fluid line connection joint (such as, for example, a Luer lock connection, not shown). The first lock flange 32a and the second lock flange 32b mutually engage, thereby preventing the rotational motion of the first enclosing component 12a and the second enclosing component 12b through the hinge 20, and thus locking the fluid line locking device 10 around the fluid line connection joint. The second lock flange 32b (and a portion of the self-locking arm 34 located immediately adjacent to the second lock flange 32b) are exposed through the lock actuation aperture 36 when the fluid line locking device 10 is in the closed configuration.

Still referring to FIG. 1F, to unlock and open the fluid line locking device 10, a user can insert a narrow implement (e.g., an ink pen) into the lock actuation aperture 36, engage the second lock flange 32b (or the portion of the self-locking arm 34 located immediately adjacent to the second lock flange 32b), and push the self-locking arm inwardly and away from the first lock flange 32a, as indicated by arrow 31 in FIG. 1F. As the self-locking arm 34 is pushed inwardly and away from the first lock flange 32a, as indicated by arrow 31, the first lock flange 32a and the second lock flange 32b will disengage, thereby allowing the rotational motion of the first enclosing component 12a and the second enclosing component 12b through the hinge 20 (see arrows 21), and thus unlocking the fluid line locking device 10 from around the fluid line connection joint.

The self-locking arm 34 is biased in the position shown in FIGS. 1F, 3A, 3B, 4A, and 4B. In this position, the first lock flange 32a and the second lock flange 32b mutually engage and prevent the rotational motion of the first enclosing component 12a and the second enclosing component 12b through the hinge 20 when the fluid line locking device 10 is in the closed configuration. The self-locking arm 34 is made of a material (described in detail below) having sufficient compliance to allow repeated elastic deformation—i.e., elastic movement of the self-locking arm inwardly and away from its biased position, as indicated by arrow 31 in FIG. 1F—without material failure.

To close and lock the fluid line locking device 10, a user places the fluid line locking device 10 around a fluid line connection joint, and rotates the first enclosing component 12a and the second enclosing component 12b through the hinge 20 until the first closure surface 16a of the first enclosing component 12a engages the second closure surface 16b of the second enclosing component 12b, thereby forming a closure joint 17. As the first closure surface 16a and the second closure surface 16b approach each other, the first oblique guiding surface 33a engages the second oblique guiding surface 33b. The engagement of the first and second oblique guiding surfaces 33a and 33b pushes the self-locking arm 34 inwardly and away from its biased position, thereby guiding the second lock flange 32b into engagement with the first lock flange 32a, which occurs when the first and second oblique guiding surfaces 33a and 33b disengage and the self-locking arm 34 elastically returns toward its biased position and the second lock flange 32b "snaps" into engagement with the first lock flange 32a.

Thus, the lock 30 operates according to an automatic self-locking snap fit mechanism in which the elastic deformation of the biased self-locking arm 34 snaps the second lock flange 32b into engagement with the first lock flange 32a as the first and second enclosing components 12a and 12b are rotated into the closed configuration through the hinge 20. As described above, the lock 30 can be manually unlocked by pushing the self-locking arm 34 inwardly and away from the first lock flange 32a until the first and second lock flanges 32a and 32b disengage (for example, using a pen or other narrow implement inserted through the lock actuation aperture 36).

The fluid line locking device 10 can further comprise a first proximal bearing surface 46a, a second proximal bearing surface 46b, a first distal bearing surface 48a, and a second distal bearing surface 48b. The first proximal bearing surface 46a and the first distal bearing surface 48a are located toward opposite longitudinal ends of the first enclosing component 12a and are separated by the first interior surface 44a. The second proximal bearing surface 46b and the second distal bearing surface 48b are located toward opposite longitudinal ends of the second enclosing component 12b and are separated by the second interior surface 44b. The use of terms "proximal" and "distal" in connection with bearing surfaces 46a, 46b, 48a, and 48b is used for convenience to describe the longitudinally opposed orientation of the bearing surfaces and should not be interpreted as requiring any specified direction of fluid flow through a fluid line connection joint enclosed and secured within the fluid line locking device 10, or any other particular orientation of the fluid line locking device 10 in use. For example, in use, fluid may flow through an enclosed and secured connection joint in a direction from the proximal end toward the distal end of the fluid line locking device 10, or fluid may flow through an enclosed and secured connection joint in a direction from the distal end toward the proximal end of the fluid line locking device 10.

The bearing surfaces 46a, 46b, 48a, and 48b are respectively offset inwardly from the interior surfaces 44a and 44b. When the fluid line locking device 10 is in the closed configuration, the first proximal bearing surface 46a and the second proximal bearing surface 46b collectively form a proximal end aperture 47. When the fluid line locking device 10 is in the closed configuration, the first distal bearing surface 48a and the second distal bearing surface 48b collectively form a distal end aperture 49. The proximal end aperture 47 and the distal end aperture 49 provide open areas through which components of a fluid line (e.g., ends of connection fittings or upstream and downstream tubing) can extend when a fluid line connection joint is enclosed and secured in the fluid line locking device 10.

The bearing surfaces 46a, 46b, 48a, and 48b also function to secure fluid line connection joints and at least portions of the constituent fittings within the interior volume of the closed fluid line locking device 10, and prevent the closed fluid line locking device 10 from moving longitudinally along the fluid line. For example, in the embodiment illustrated in FIGS. 1A-4B, the proximal bearing surfaces 46a and 46b are structured and dimensioned to secure a standard male Luer lock fitting within the interior volume of the closed fluid line locking device 10, and the distal bearing surfaces 48a and 48b are structured and dimensioned to secure a standard female Luer lock fitting within the interior volume of the closed fluid line locking device 10. Thus, the bearing surfaces 46a, 46b, 48a, and 48b (and the illustrated embodiment of the fluid line locking device 10 generally) are structured and dimensioned to secure a standard Luer lock fluid line connection.

Luer lock connections are used extensively in medical and laboratory applications. Luer lock connections comprise mutually engaging male and female conical fittings with a 6% taper and threads/lugs that threadably attach the fittings together. The structure and dimensions of Luer lock connections are standardized by International Standard ISO 594/1, first edition—1986 ("Conical fittings with a 6% (Luer) taper for syringes, needles and certain other medical equipment—Part 1: General requirements"), and International Standard ISO 594/2, second edition—1998 ("Conical fittings with a 6% (Luer) taper for syringes, needles and certain other medical equipment—Part 2: Lock fittings"), which are incorporated by reference into this specification.

Figure 5A:
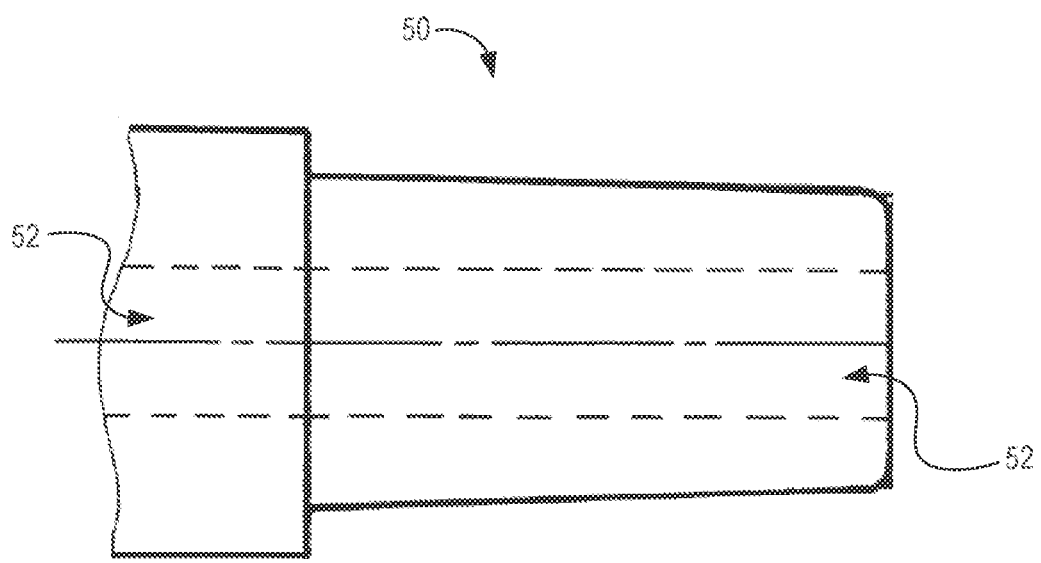
FIG. 5A is a schematic side view of a standard male Luer fitting.
Figure 5B:
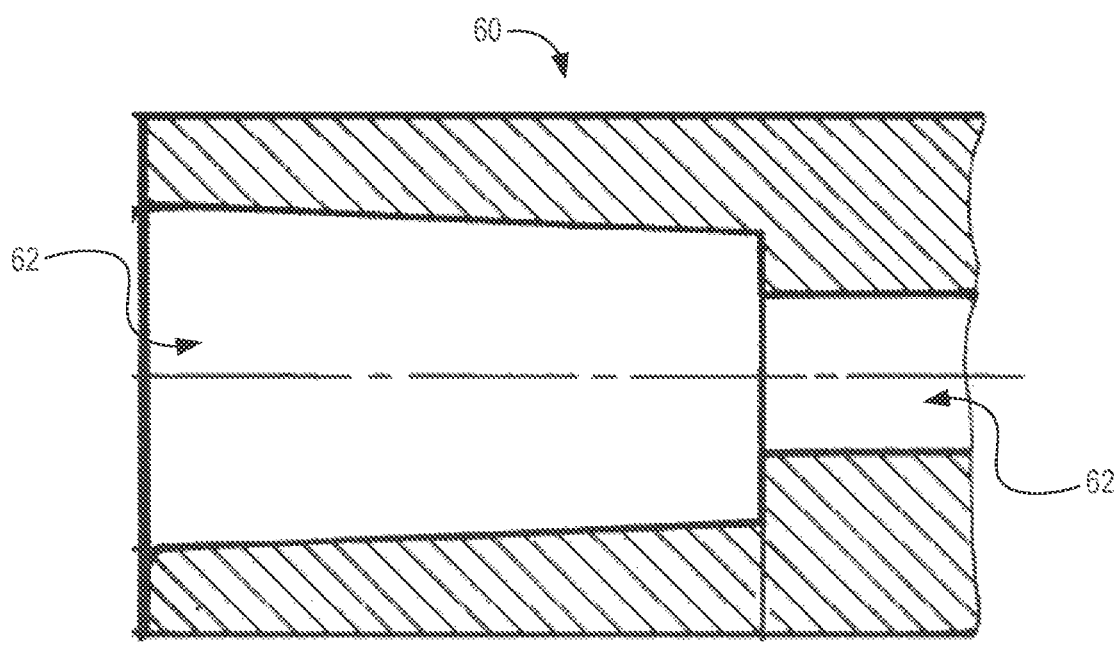
FIG. 5B is a schematic cross-sectional side view of a standard female Luer fitting.
Figure 5C:
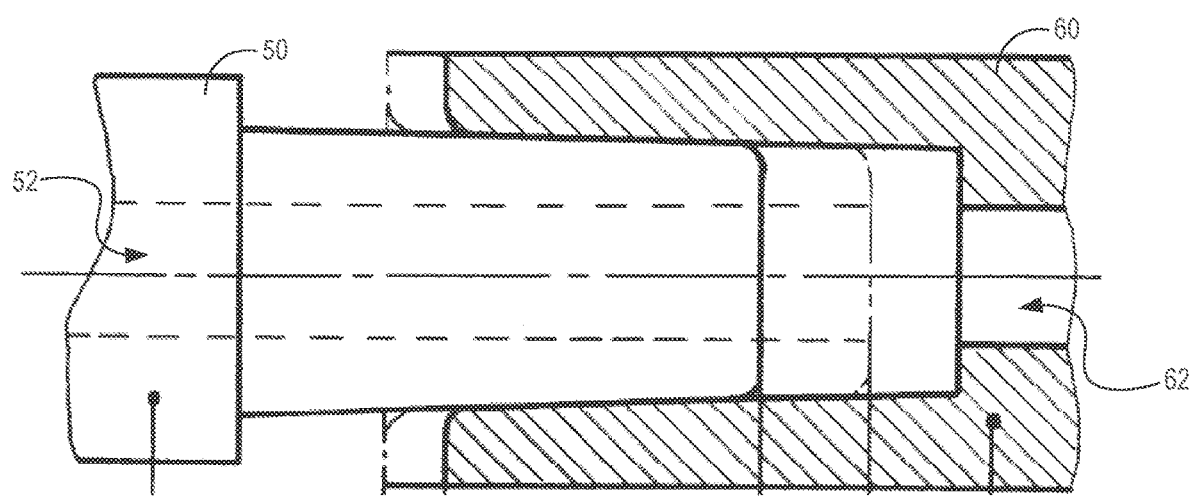
FIG. 5C is a schematic partial cross-sectional side view of a standard male Luer fitting engaged with a standard female Luer fitting.
Figure 6A:
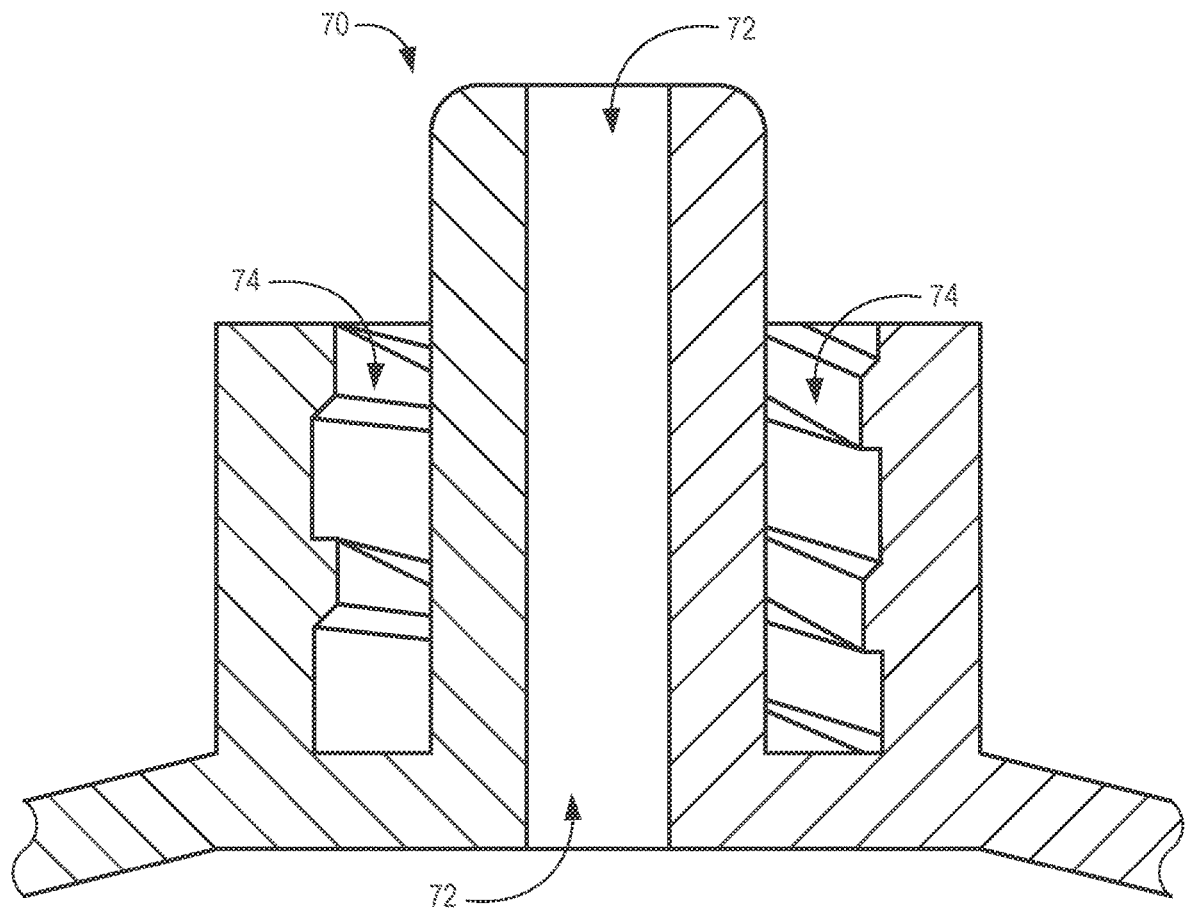
FIG. 6A is a schematic cross-sectional side view of a standard male Luer lock fitting with a fixed, internally-threaded collar.
Figure 6B:
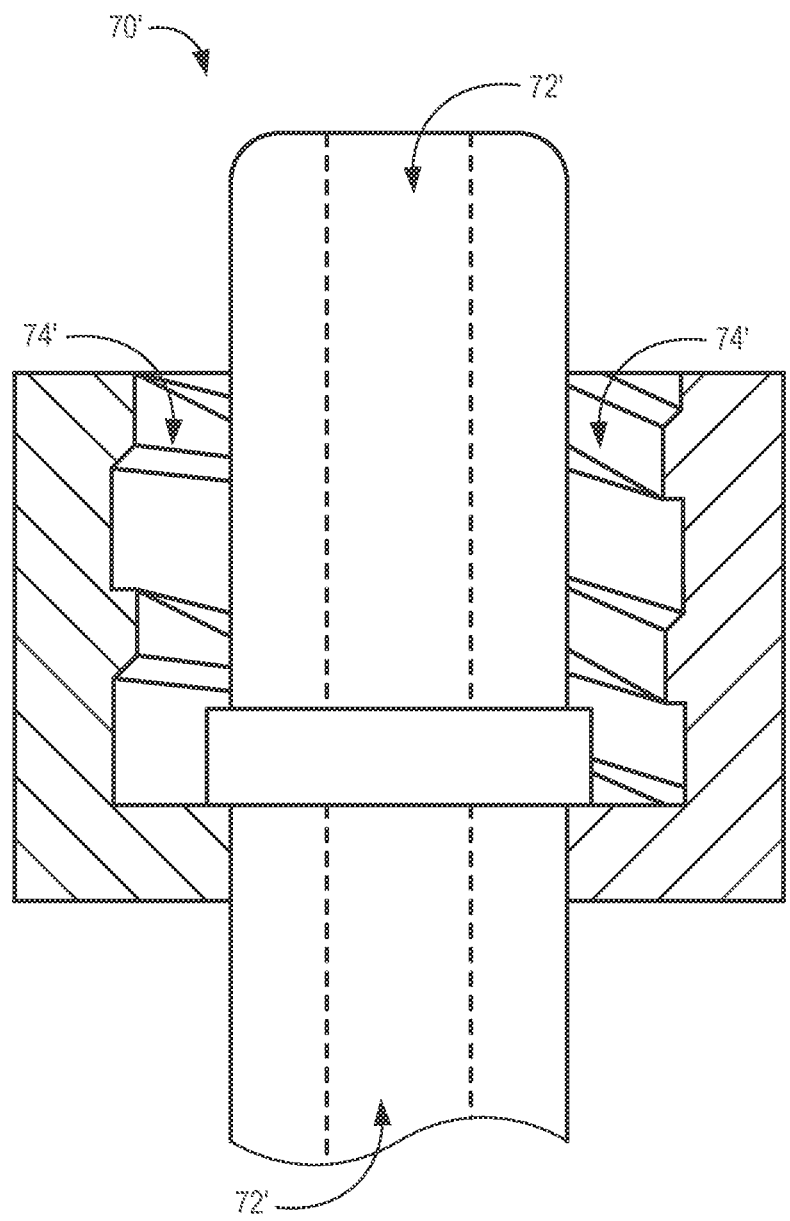
FIG. 6B is schematic partial cross-sectional side view of a standard male Luer lock fitting with a rotatable, internally-threaded collar.
Figure 6C:
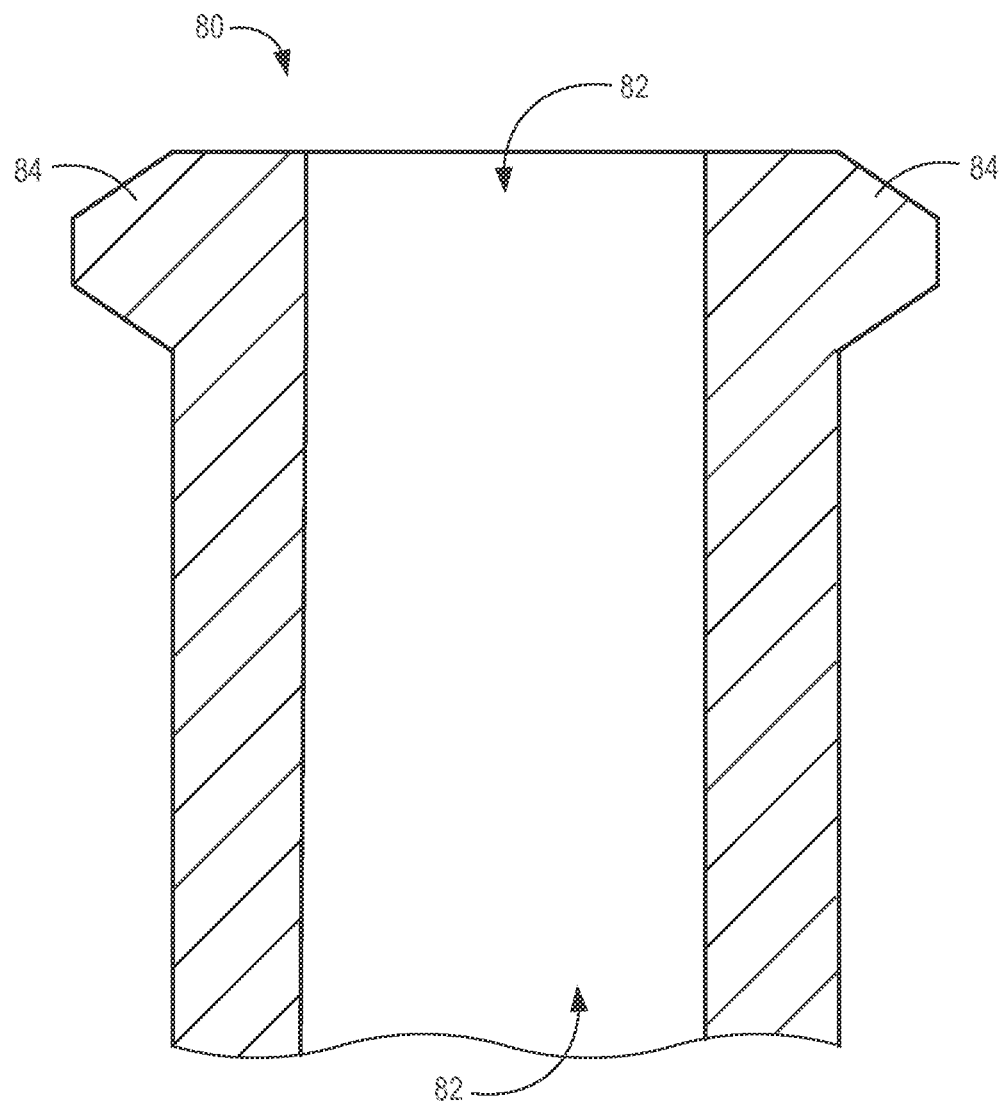
FIG. 6C is a schematic cross-sectional side view of a standard female Luer lock fitting with external threading lugs.
Figure 6D:
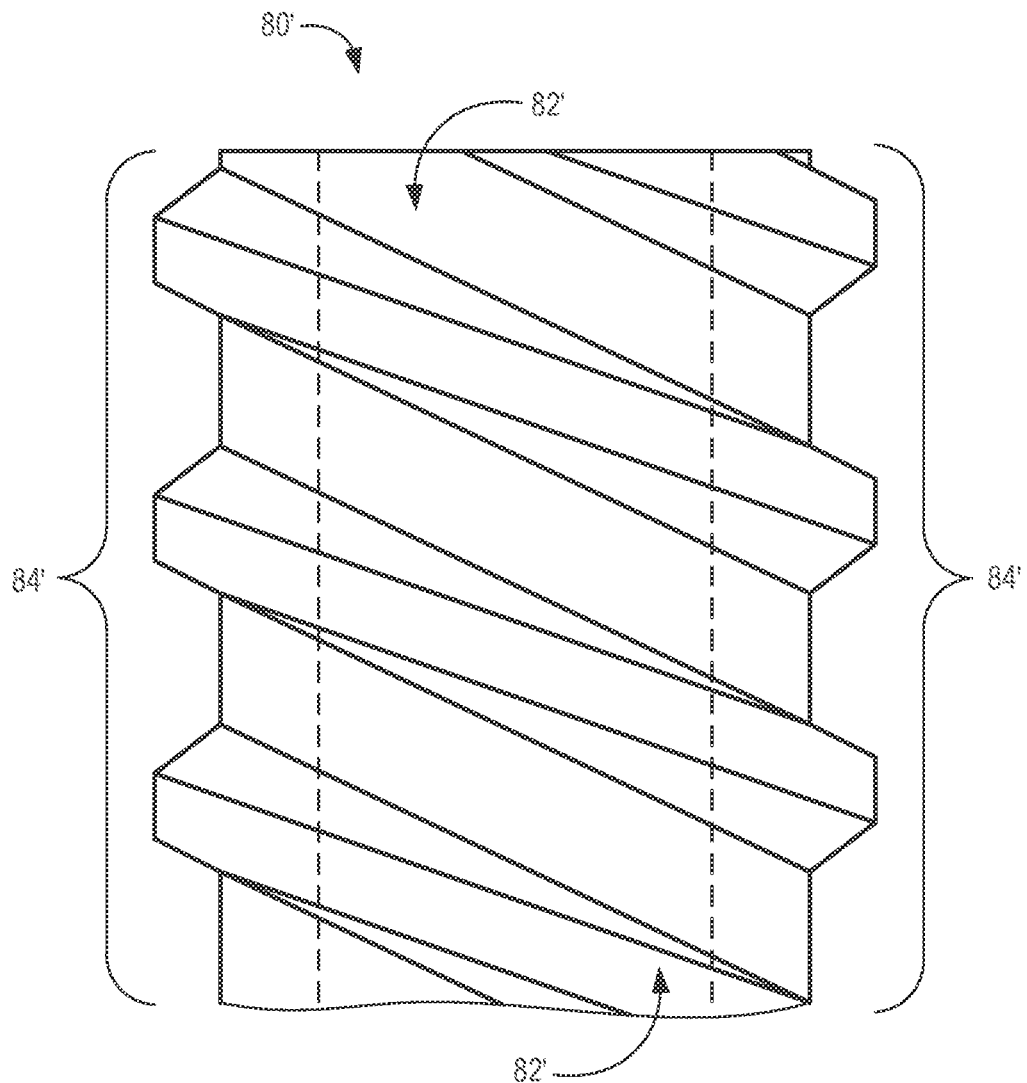
FIG. 6D is a schematic side view of a standard female Luer lock fitting with external threads.

FIG. 5A shows a standard male Luer fitting 50 comprising a fluid conduit 52, FIG. 5B shows a standard female Luer fitting 60 comprising a fluid conduit 62, and FIG. 5C shows a Luer connection between the standard male and female Luer fittings. Referring to FIG. 6A, a standard male Luer lock fitting 70 comprises a fluid conduit 72 through the conical fitting and a fixed, internally-threaded collar 74. Similarly, referring to FIG. 6B, another standard male Luer lock fitting 70' comprises a fluid conduit 72' through the conical fitting and a rotatable, internally-threaded collar 74'. Referring to FIG. 6C, a standard female Luer lock fitting 80 comprises a conical fluid conduit 82 and thread lugs 84 located on the exterior cylindrical surface of the fitting. Similarly, referring to FIG. 6D, another standard female. Luer lock fitting 80' comprises a conical fluid conduit 82' and threads 84' located on the exterior cylindrical surface of the fitting. The exterior lugs 84 and the exterior threads 84' of the female Luer lock fittings 80 and 80' can engage with the interior threads 74 and 74' of the male Luer lock fittings 70 and 70' to provide Luer lock connections.

Although standard Luer lock connections generally provide fluid impervious seals between the male and female fittings, and are generally resistant to unthreading and unintentional disengagement, it is nevertheless beneficial to provide an additional locking mechanism for Luer lock connections in certain applications, such as, for example, in central lines and other catheter lines, particularly in pediatric patients. Accordingly, the fluid line locking devices described in this specification may be implemented to enclose and secure standard Luer lock connections.

Figure 7A:
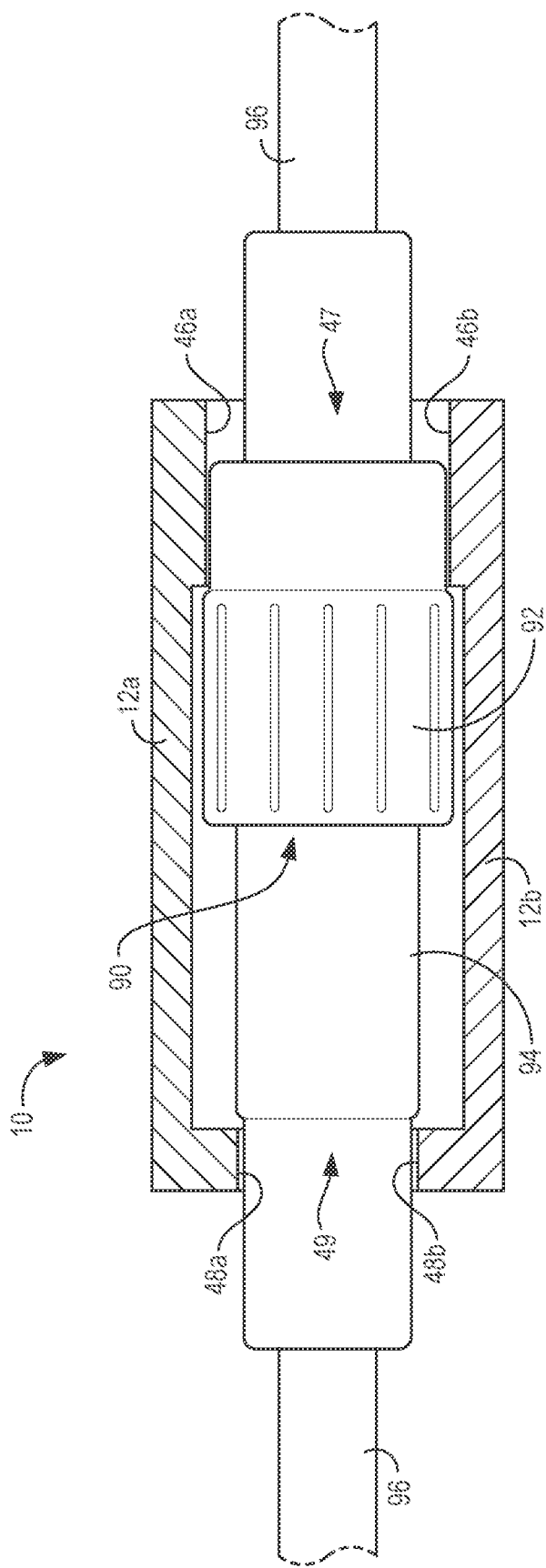
FIG. 7A is schematic partial cross-sectional side view of the fluid line locking device shown in FIGS. 1A-1F engaging and enclosing a standard Luer lock connection.
Figure 7B:
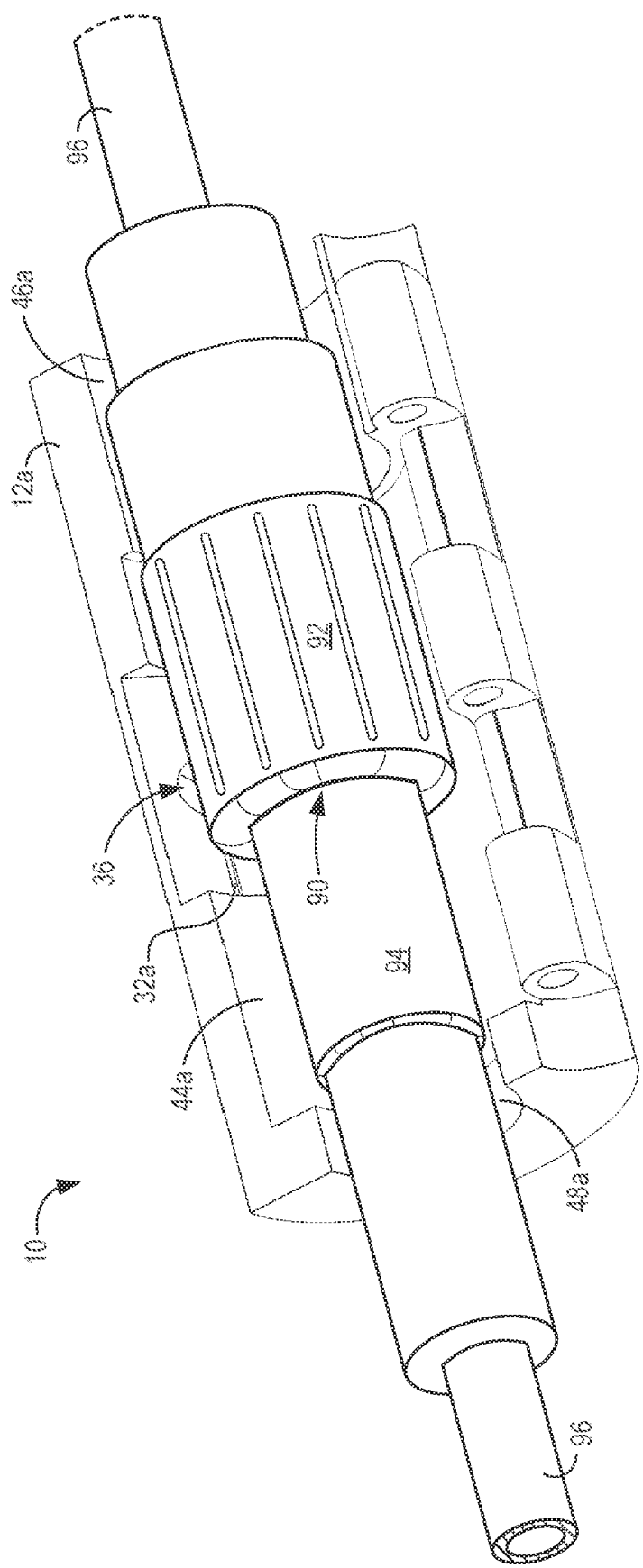
FIG. 7B is a side perspective view of the first enclosing component of the fluid line locking device shown in FIGS. 1A-1F engaging a standard Luer lock connection.

Referring to FIGS. 7A and 7B, the fluid line locking device 10 is shown engaging with, enclosing, and securing a standard Luer lock connection 90. The standard Luer lock connection 90 comprises a standard male Luer lock fitting 92 threaded to a standard female Luer lock fitting 94. The standard male Luer lock fitting 92 and the standard female Luer lock fitting 94 each have tubing 96 respectively attached to the non-threaded ends of the fittings. The tubing 96 attached to the standard male Luer lock fitting 92 may be connected to an IV source, for example. The tubing 96 attached to the standard female Luer lock fitting 94 may be connected to a catheter inserted into a medical patient, for example. The standard Luer lock connection 90 is positioned within the interior volume of the closed fluid line locking device 10. The non-threaded end of the standard male Luer lock fitting 92 extends through the proximal end aperture 47 of the fluid line locking device 10. The non-threaded end of the standard female Luer lock fitting 94 extends through the distal end aperture 49 of the fluid line locking device 10.

The proximal bearing surfaces 46a and 46b secure the standard male Luer lock fitting 92 within the interior volume of the closed fluid line locking device 10, and the distal bearing surfaces 48a and 48b secure the standard female Luer lock fitting 94 within the interior volume of the closed fluid line locking device 10. Thus, the bearing surfaces 46a, 46b, 48a, and 48b secure the standard Luer lock connection 90 within the closed fluid line locking device 10 and prevent the fluid line locking device 10 from moving longitudinally along the fluid line formed by the tubing 96.

In addition to enclosing and securing fluid line connection joints, the fluid line locking devices described in this specification may be used to enclose and secure fluid line caps. For example, in central line and other catheter applications employing standard Luer lock connections, disinfectant caps may be threaded onto standard female Luer lock fittings, and disinfectant tips may be threaded into standard male Luer lock fittings, when such fittings are not threaded together in a Luer lock connection (e.g., when a patient's central line is disconnected from an IV source). Disinfectant caps and tips contain a disinfecting agent such as isopropyl alcohol that contacts the surfaces of the Luer fittings and kills infectious bacteria. Disinfectant caps and tips designed for standard Luer lock fittings are available from a number of suppliers and include, for example, Curos™ Disinfecting Caps and Tips, available from 3M Health Care/Ivera Medical Corporation, and Kendall™ Disinfectant Caps, available from Covidien AG. Disinfectant caps are also described in U.S. Pat. Nos. 7,780,794; 7,985,302; 8,206,514; and D607,325, which are incorporated by reference into this specification.

Figure 7D:
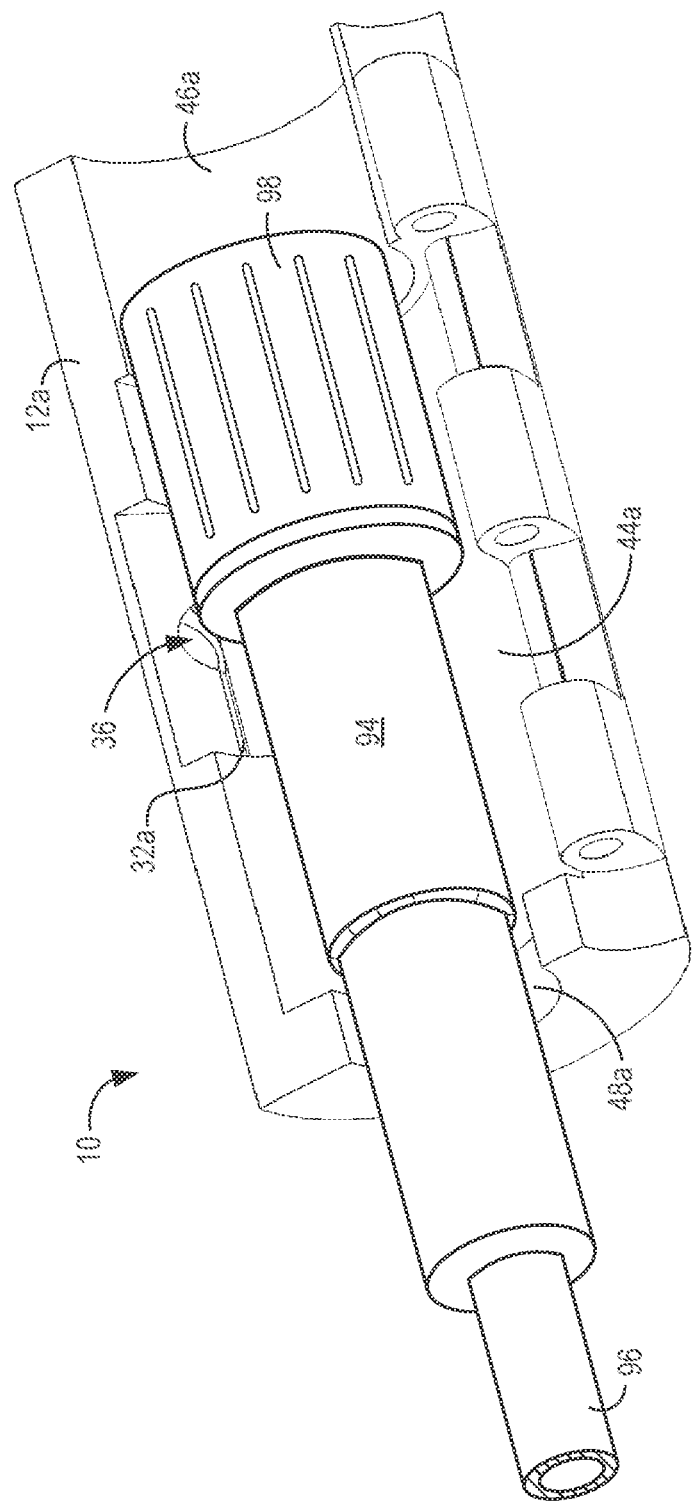
FIG. 7D is a side perspective view of the first enclosing component of the fluid line locking device shown in FIGS. 1A-1F engaging a female Luer lock fitting and an attached disinfectant cap.

Referring to FIGS. 7C and 7D, the fluid line locking device 10 is shown engaging with, enclosing, and securing a disinfectant cap 98 threaded onto a standard female Luer lock fitting 94. The non-threaded end of the standard female Luer lock fitting 94 extends through the distal end aperture 49 of the fluid line locking device 10. The disinfectant cap 98 is contained within the interior volume of the fluid line locking device 10. The distal bearing surfaces 48a and 48b secure the standard female Luer lock fitting 94 within the interior volume of the closed fluid line locking device 10. The proximal bearing surfaces 46a and 46b secure the disinfectant cap 98 within the interior volume of the closed fluid line locking device 10. Thus, the bearing surfaces 46a, 46b, 48a, and 48b secure the capped standard female Luer lock connection 94 within the closed fluid line locking device 10, and prevent the fluid line locking device 10 from moving longitudinally along the fluid line formed by the tubing 96 and from disengaging from the capped end of the standard female Luer lock connection 94.

Referring to FIGS. 8A, 8B, 9, and 10, a fluid line locking device 110, similar to the fluid line locking device 10 shown in FIGS. 1A-1F, comprises extended hinge walls 118a and 118b that isolate a hinge 120 from the interior volume of the closed fluid line locking device 110.

The fluid line locking device 110 comprises a first enclosing component 112a and a second enclosing component 112b. The first enclosing component 112a comprises a first enclosing wall 114a, and the second enclosing component 112b comprises a second enclosing wall 114b. The first enclosing component 112a and the second enclosing component 112b are connected to each other through the hinge 120. The first enclosing component 112a and the second enclosing component 112b are hemi-cylindrical enclosing components that together form the fluid line locking device 110 comprising a cylindrical exterior structure with the hinge 120 located along the length dimension of the cylinder. The longitudinal location of the hinge 120 allows the fluid line locking device 110 to open and close in a "clamshell" manner, as illustrated by arrows 121, wherein the first enclosing component 112a and the second enclosing component 112b rotate around the pin 124 of the hinge 120.

Although the embodiments shown in FIGS. 8A-10 comprise an exterior cylindrical structure, it is nevertheless understood that the first exterior surface 142a of the first enclosing component 112a, and the second exterior surface 142b of the second enclosing component 112b, can independently comprise any shapes or contours. For example, instead of the cylindrical exterior structure, the fluid line locking device 110 can comprise a hexagonal cross-section, an octagonal cross-section, or any other cross-sectional shape perpendicular to the longitudinal axis of the device.

The hinge 120 of the fluid line locking device 110 comprises a butt-mortise hinge wherein intermeshing knuckles 122a and 122b form the barrel of the hinge, and the pin 124 is located within the barrel and through the intermeshed knuckles 122a and 122b. The first knuckles 122a are integrally formed in the first enclosing wall 114a of the first enclosing component 112a, and are mortised flush with the first exterior surface 142a of the first enclosing component 112a. The first knuckles 122a are separated from the interior volume of the closed fluid line locking device 110 by extended hinge walls 118a and 118b. The second knuckles 22b are integrally formed in the second enclosing wall 114b of the second enclosing component 112b, and are mortised flush with the second exterior surface 142b of the second enclosing component 112b. The second knuckles 22b are separated from the interior volume of the closed fluid line locking device 110 by extended hinge walls 118a and 118b.

The separation of the hinge 120 from the interior volume of the closed fluid line locking device 110 by extended hinge walls 118a and 118b isolates the hinge and can prevent liquids from infiltrating through the hinge 120 and into or out of the interior volume of the closed fluid line locking device 110.

Figure 8A:
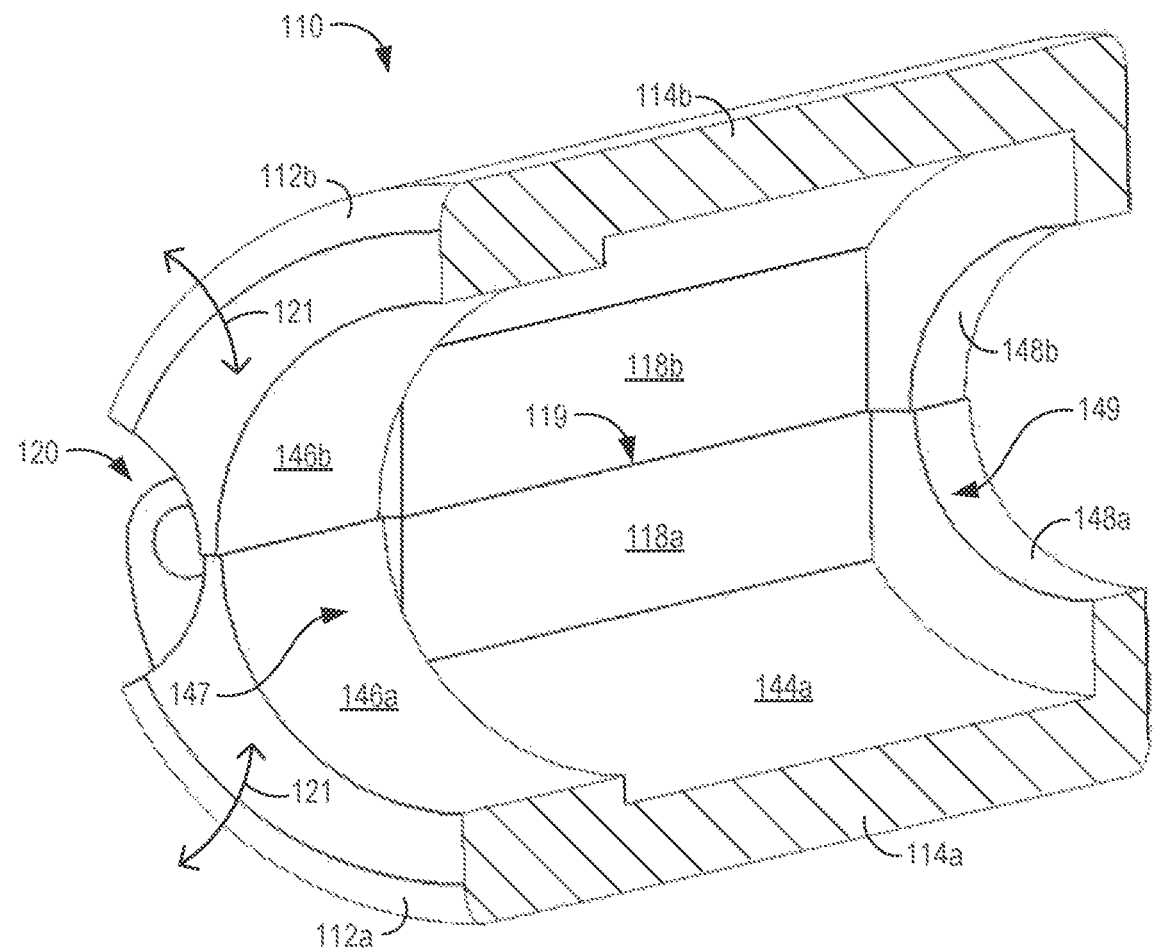
FIG. 8A is a cross-sectional side perspective views of a fluid line locking device, similar to the device shown in FIGS. 1A-1F, and comprising extended hinge walls.
Figure 8B:
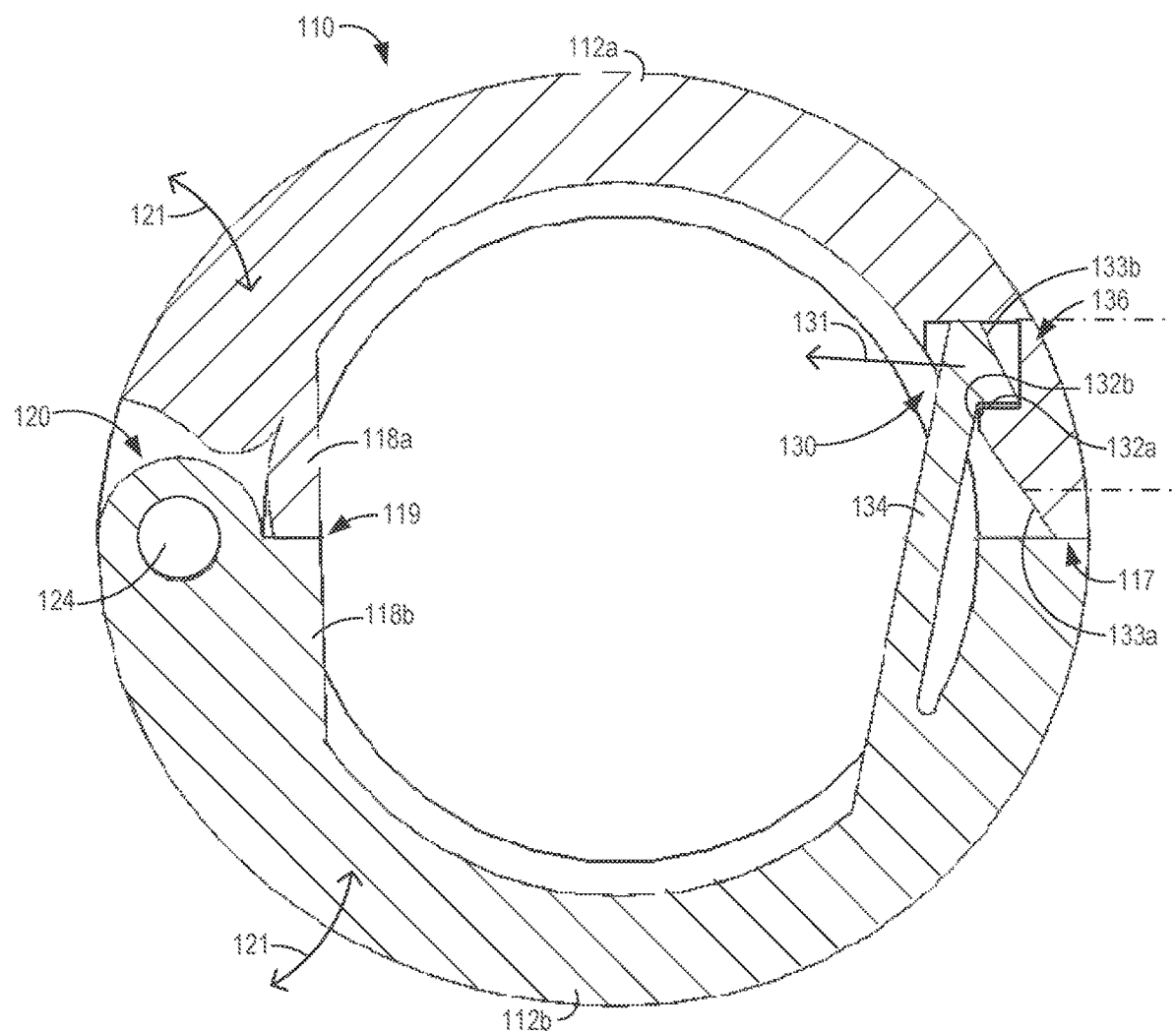
FIG. 8B is a cross-sectional end view of the fluid line locking device shown in FIG. 8A.
Figure 9:
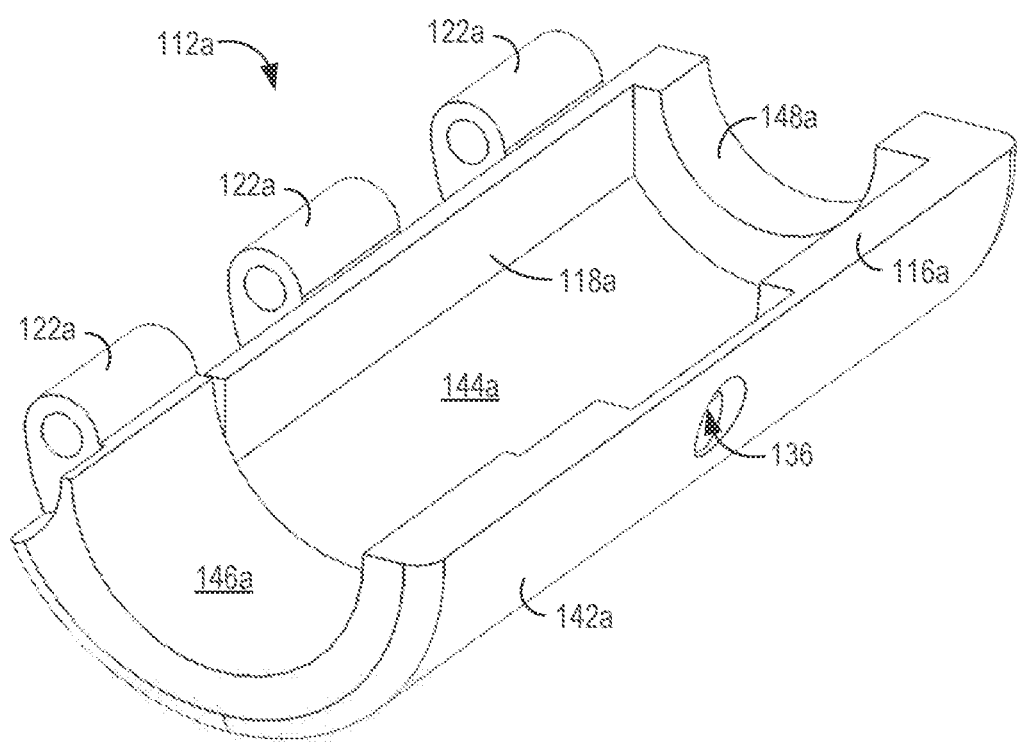
FIG. 9 is a side perspective view of the first enclosing component of the fluid line locking device shown in FIGS. 8A and 8B.

The fluid line locking device 110 comprises a lock 130 that secures the first enclosing component 112a and the second enclosing component 112b in the closed configuration shown in FIGS. 8A and 8B. The lock 130 comprises a first lock flange 132a formed in the first interior surface 144a of the first enclosing component 112a. The first lock flange 132a is located adjacent to a first oblique guiding surface 133a. The lock 130 also comprises a second lock flange 132b located on a self-locking arm 134. The self-locking arm 134 is located on the second interior surface 144b of the second enclosing component 112b. The self-locking arm 134 is integrally formed with the second enclosing wall 114b of the second enclosing component 112b. The second lock flange 132b is located on the self-locking arm 134 adjacent to a second oblique guiding surface 133b. The lock 130 also comprises a lock actuation aperture 136 extending from the first exterior surface 142a of the first enclosing component 112a, through the first enclosing wall 114a, through the first lock flange 132a formed in the first interior surface 144a, and to the interior volume of the fluid line locking device 110.

Referring to FIG. 8B, in operation, the fluid line locking device 110 is in a closed configuration, as shown, and encloses and secures a fluid line connection joint (such as, for example, a Luer lock connection, not shown). The first lock flange 132a and the second lock flange 132b mutually engage, thereby preventing the rotational motion of the first enclosing component 112a and the second enclosing component 112b through the hinge 120, and thus locking the fluid line locking device 110 around the fluid line connection joint. The second lock flange 132b (and a portion of the self-locking arm 134 located immediately adjacent to the second lock flange 132b) are exposed through the lock actuation aperture 136 when the fluid line locking device 110 is in the closed configuration.

Still referring to FIG. 8B, to unlock and open the fluid line locking device 110, a user can insert a narrow implement (e.g., an ink pen) into the lock actuation aperture 136, engage the second lock flange 132b (or the portion of the self-locking arm 134 located immediately adjacent to the second lock flange 132b), and push the self-locking arm inwardly and away from the first lock flange 132a, as indicated by arrow 131 in FIG. 8B. As the self-locking arm 134 is pushed inwardly and away from the first lock flange 132a, as indicated by arrow 131, the first lock flange 132a and the second lock flange 132b will disengage, thereby allowing the rotational motion of the first enclosing component 112a and the second enclosing component 112b through the hinge 120 (see arrows 121), and thus unlocking the fluid line locking device 110 from around the fluid line connection joint.

Figure 10:
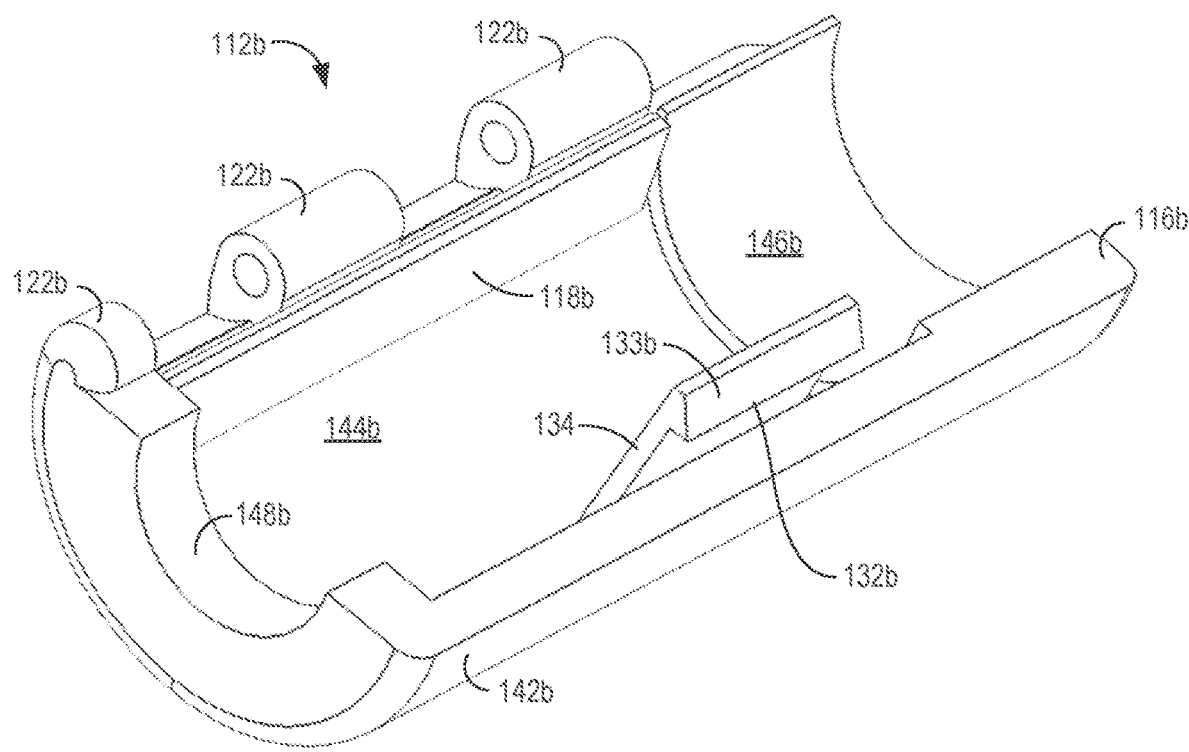
FIG. 10 is a side perspective view of the second enclosing component of the fluid line locking device shown in FIGS. 8A and 8B.

The self-locking arm 134 is biased in the position shown in FIGS. 8B and 10. In this position, the first lock flange 132a and the second lock flange 132b mutually engage and prevent the rotational motion of the first enclosing component 112a and the second enclosing component 112b through the hinge 120 when the fluid line locking device 110 is in the closed configuration. The self-locking arm 134 is made of a material (described in detail below) having sufficient compliance to allow repeated elastic deformation—i.e., elastic movement of the self-locking arm inwardly and away from its biased position, as indicated by arrow 131 in FIG. 8B—without material failure.

To close and lock the fluid line locking device 110, a user places the fluid line locking device 110 around a fluid line connection joint, and rotates the first enclosing component 112a and the second enclosing component 112b through the hinge 120 until the first closure surface 116a of the first enclosing component 112a engages the second closure surface 116b of the second enclosing component 112b, thereby forming a closure joint 117. Similarly, as a user rotates the first enclosing component 112a and the second enclosing component 112b through the hinge 120, the first extended hinge wall 118a approaches and engages the second extended hinge wall 118b, thereby forming a closure joint 119. As the first closure surface 116a and the second closure surface 116b approach each other, the first oblique guiding surface 133a engages the second oblique guiding surface 133b. The engagement of the first and second oblique guiding surfaces 133a and 133b pushes the self-locking arm 134 inwardly and away from its biased position, thereby guiding the second lock flange 132b into engagement with the first lock flange 132a, which occurs when the first and second oblique guiding surfaces 133a and 133b disengage and the self-locking arm 134 elastically returns toward its biased position and the second lock flange 132b "snaps" into engagement with the first lock flange 132a.

Thus, the lock 130 operates according to an automatic self-locking snap fit mechanism in which the elastic deformation of the biased self-locking arm 134 snaps the second lock flange 132b into engagement with the first lock flange 132a as the first and second enclosing components 112a and 112b are rotated into the closed configuration through the hinge 120. As described above, the lock 130 can be manually unlocked by pushing the self-locking arm 134 inwardly and away from the first lock flange 132a until the first and second lock flanges 132a and 132b disengage (for example, using a pen or other narrow implement inserted through the lock actuation aperture 136).

The fluid line locking device 110 can further comprise a first proximal bearing surface 146a, a second proximal bearing surface 146b, a first distal bearing surface 148a, and a second distal bearing surface 148b. The first proximal bearing surface 146a and the first distal bearing surface 148a are located toward opposite longitudinal ends of the first enclosing component 112a and are separated by the first interior surface 144a. The second proximal bearing surface 146b and the second distal bearing surface 148b are located toward opposite longitudinal ends of the second enclosing component 112b and are separated by the second interior surface 144b.

The bearing surfaces 146a, 146b, 148a, and 148b are respectively offset inwardly from the interior surfaces 144a and 144b. When the fluid line locking device 110 is in the closed configuration, the first proximal bearing surface 146a and the second proximal bearing surface 146b collectively form a proximal end aperture 147. When the fluid line locking device 110 is in the closed configuration, the first distal bearing surface 148a and the second distal bearing surface 148b collectively form a distal end aperture 149. The proximal end aperture 147 and the distal end aperture 149 provide open areas through which components of a fluid line (e.g., ends of connection fittings or upstream and downstream tubing) can extend when a fluid line connection joint is enclosed and secured in the fluid line locking device 110.

The bearing surfaces 146a, 146b, 148a, and 148b also function to secure fluid line connection joints and at least portions of the constituent fittings within the interior volume of the closed fluid line locking device 110, and prevent the closed fluid line locking device 110 from moving longitudinally along the fluid line. For example, in the embodiment illustrated in FIGS. 8A-10, the proximal bearing surfaces 416a and 146b are structured and dimensioned to secure a standard male Luer lock fitting within the interior volume of the closed fluid line locking device 110, and the distal bearing surfaces 148a and 148b are structured and dimensioned to secure a standard female Luer lock fitting within the interior volume of the closed fluid line locking device 110. Thus, the bearing surfaces 146a, 146b, 148a, and 148b (and the illustrated embodiment of the fluid line locking device 110 generally) are structured and dimensioned to secure a standard Luer lock fluid line connection.

The embodiments of a fluid line locking device shown in FIGS. 1A-4B and 8A-10 comprise a butt-mortise hinge. However, it is understood that fluid line locking devices in accordance with this specification may comprise different types of hinges, such as, for example, a living hinge.

Figure 11A:
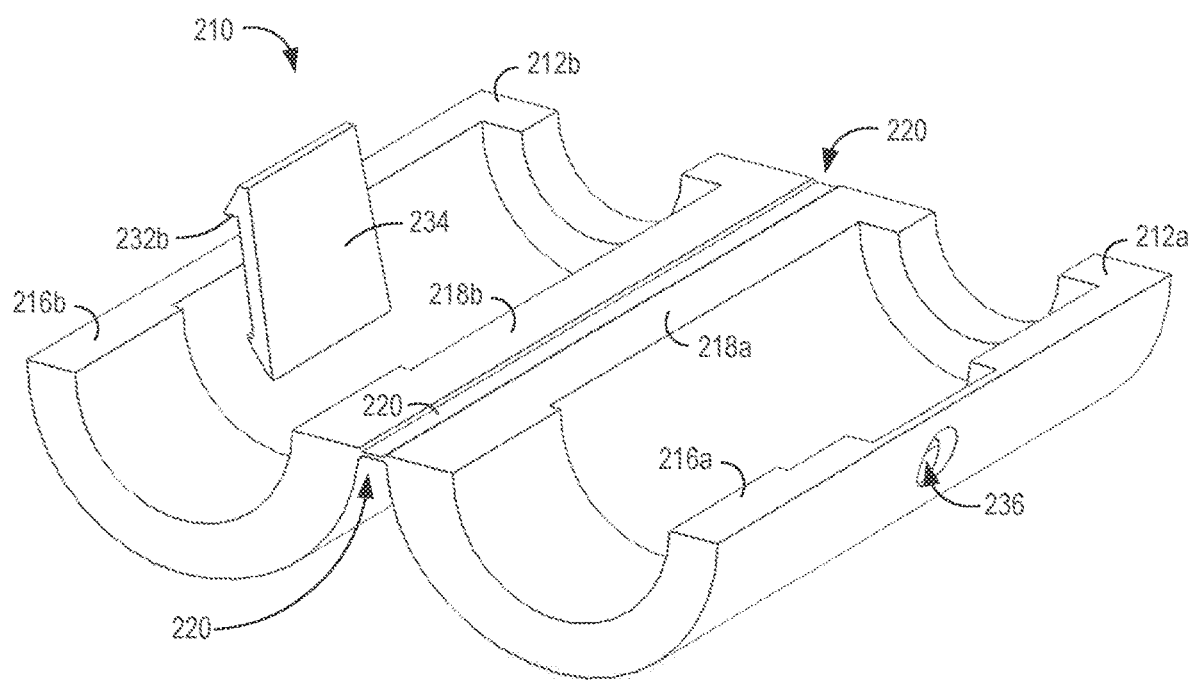
FIGS. 11A and 11B are side perspective views of a fluid line locking device, similar to the device shown in FIGS. 1A-1F, 9A, and 9B, and comprising a living hinge connecting the first enclosing component and the second enclosing component.
Figure 11B:
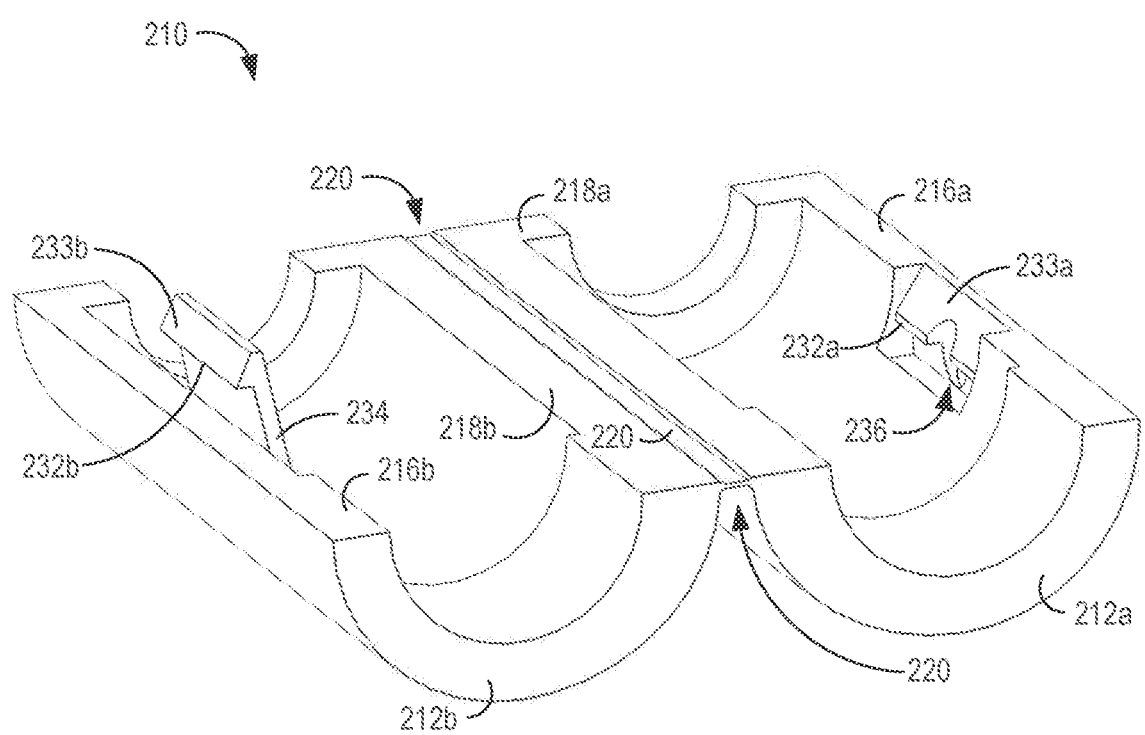
Figure 11C:
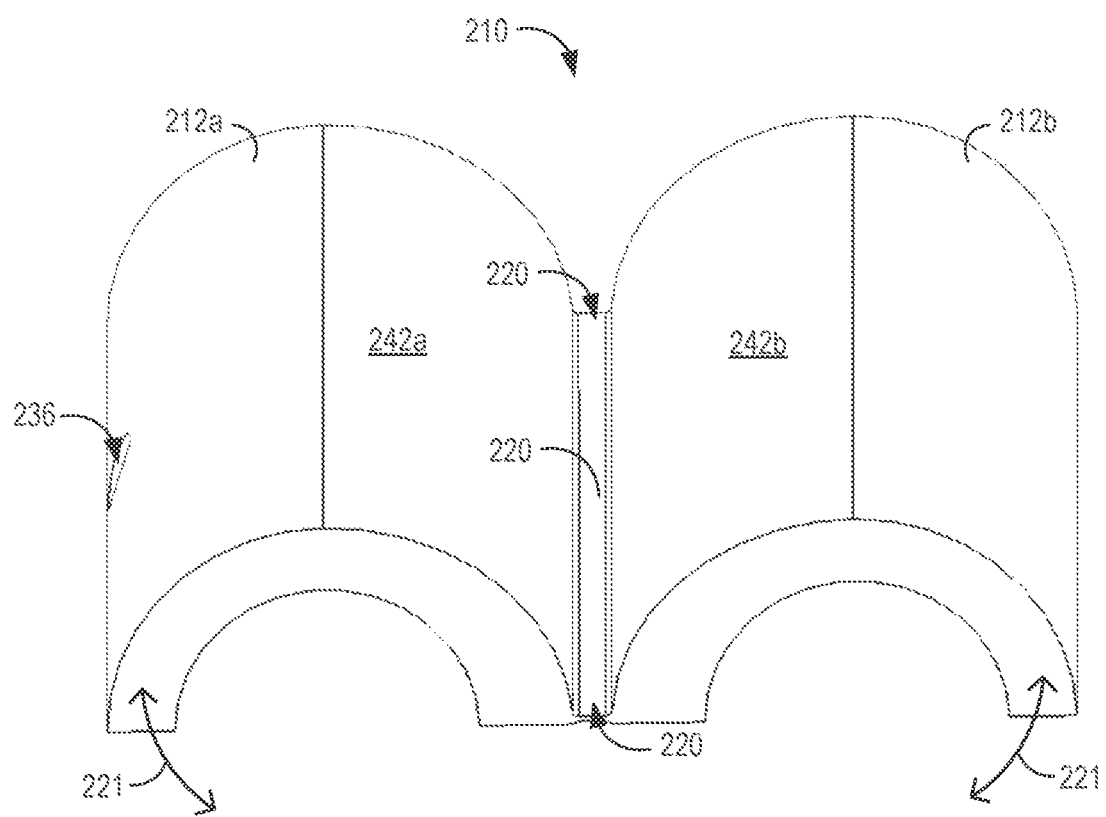
FIG. 11C is bottom perspective view of the fluid line locking device shown in FIGS. 11A and 11B.

Referring to FIGS. 11A-11C, a fluid line locking device 210, similar to the fluid line locking devices 10 and 110, described above, comprises a living hinge 220 that connects the first enclosing component 212a and the second enclosing component 212b. The living hinge 220 comprises a relatively thin, flexible, and continuous piece of material integral with the material forming the first enclosing component 212a and the second enclosing component 212b. The living hinge 220 connects to the first enclosing component 212a at the intersection of a first exterior surface 242a and a first hinge closure surface 218a. The living hinge 220 connects to the second enclosing component 212b at the intersection of a second exterior surface 242b and a second hinge closure surface 218b. The living hinge 220 is separated from the interior volume of the closed fluid line locking device 210 by a closure joint formed when the first hinge closure surface 218a engages with the second hinge closure surface 218b as the first enclosing component 212a and the second enclosing component 212b are rotated into a closed configuration.

The first enclosing component 212a and the second enclosing component 212b are hemi-cylindrical enclosing components that together form the fluid line locking device 210 comprising a cylindrical exterior structure with the living hinge 220 located along the length dimension of the cylinder. The longitudinal location of the living hinge 220 allows the fluid line locking device 210 to open and close in a "clamshell" manner, as illustrated by arrows 221, wherein the first enclosing component 212a and the second enclosing component 212b rotate around the longitudinal axis of the living hinge 220.

Although the embodiments shown in FIGS. 11A-11C comprise an exterior cylindrical structure, it is nevertheless understood that the first exterior surface 242a of the first enclosing component 212a, and the second exterior surface 242b of the second enclosing component 212b, can independently comprise any shapes or contours. For example, instead of the cylindrical exterior structure, the fluid line locking device 210 can comprise a hexagonal cross-section, an octagonal cross-section, or any other cross-sectional shape perpendicular to the longitudinal axis of the device.

The fluid line locking device 210 comprises a lock that secures the first enclosing component 212a and the second enclosing component 212b in the closed configuration. The lock comprises a first lock flange 232a formed in the interior surface of the first enclosing component 112a. The first lock flange 232a is located adjacent to a first oblique guiding surface 233a. The lock also comprises a second lock flange 232b located on a self-locking arm 234. The self-locking arm 234 is located on the interior surface of the second enclosing component 212b. The self-locking arm 234 is integrally formed with the wall of the second enclosing component 212b. The second lock flange 232b is located on the self-locking arm 234 adjacent to a second oblique guiding surface 233b. The lock also comprises a lock actuation aperture 236 extending from the first exterior surface 242a of the first enclosing component 212a, through the wall of the first enclosing component 212a, through the first lock flange 232a, and to the interior volume of the fluid line locking device 210.

Like as described above, in operation, the fluid line locking device 210 is in a closed configuration, and encloses and secures a fluid line connection joint (such as, for example, a Luer lock connection, not shown). The first lock flange 232a and the second lock flange 232b mutually engage, thereby preventing the rotational motion of the first enclosing component 212a and the second enclosing component 212b through the living hinge 220, and thus locking the fluid line locking device 210 around the fluid line connection joint. The second lock flange 232b (and a portion of the self-locking arm 234 located immediately adjacent to the second lock flange 232b) are exposed through the lock actuation aperture 236 when the fluid line locking device 210 is in the closed configuration.

To unlock and open the fluid line locking device 210, a user can insert a narrow implement (e.g., an ink pen) into the lock actuation aperture 236, engage the second lock flange 232b (or the portion of the self-locking arm 234 located immediately adjacent to the second lock flange 232b), and push the self-locking arm inwardly and away from the first lock flange 232a. As the self-locking arm 234 is pushed inwardly and away from the first lock flange 232a, the first lock flange 232a and the second lock flange 232b will disengage, thereby allowing the rotational motion of the first enclosing component 212a and the second enclosing component 212b through the hinge 220, and thus unlocking the fluid line locking device 210 from around the fluid line connection joint.

The self-locking arm 234 is biased in the locked position in which the first lock flange 232a and the second lock flange 232b mutually engage and prevent the rotational motion of the first enclosing component 212a and the second enclosing component 212b through the living hinge 220 when the fluid line locking device 210 is in the closed configuration. The self-locking arm 234 is made of a material (described in detail below) having sufficient compliance to allow repeated elastic deformation—i.e., elastic movement of the self-locking arm inwardly and away from its biased position without material failure.

To close and lock the fluid line locking device 210, a user places the fluid line locking device 210 around a fluid line connection joint, and rotates the first enclosing component 212a and the second enclosing component 212b through the living hinge 220 until the first closure surface 216a of the first enclosing component 212a engages the second closure surface 216b of the second enclosing component 212b, thereby forming a closure joint 117. Similarly, as a user rotates the first enclosing component 212a and the second enclosing component 212b through the living hinge 220, the first hinge closure surface 218a approaches and engages the second hinge closure surface 218b, thereby forming another closure joint. As the first closure surface 216a and the second closure surface 216b approach each other, the first oblique guiding surface 233a engages the second oblique guiding surface 233b. The engagement of the first and second oblique guiding surfaces 233a and 233b pushes the self-locking arm 234 inwardly and away from its biased position, thereby guiding the second lock flange 232b into engagement with the first lock flange 232a, which occurs when the first and second oblique guiding surfaces 233a and 233b disengage and the self-locking arm 234 elastically returns toward its biased position and the second lock flange 232b "snaps" into engagement with the first lock flange 232a.

Thus, the lock operates according to an automatic self-locking snap fit mechanism in which the elastic deformation of the biased self-locking arm 234 snaps the second lock flange 232b into engagement with the first lock flange 232a as the first and second enclosing components 212a and 212b are rotated into the closed configuration through the living hinge 220. As described above, the lock can be manually unlocked by pushing the self-locking arm 234 inwardly and away from the first lock flange 232a until the first and second lock flanges 232a and 232b disengage (for example, using a pen or other narrow implement inserted through the lock actuation aperture 236).

Although not labeled in FIGS. 11A-11C, like the embodiments described above, the fluid line locking device 210 further comprises proximal bearing surfaces and distal bearing surfaces located toward opposite longitudinal ends of the enclosing components and separated by the first interior surfaces of the enclosed components. The bearing surfaces can be structured and dimensioned to secure a standard Luer lock fluid line connection The fluid line locking devices described in this specification can comprise a plastic material of construction such as, for example, polyethylene, polypropylene, polycarbonate, or polyamide. In various embodiments, the fluid line locking device may comprise a plastic material of construction that is transparent to visible light so that users can view a fluid line connection joint enclosed and secured within the fluid line locking device. The constituent enclosing components, including all of the internal features and characteristics, of the fluid line locking devices described in this specification can be produced, for example, by injection molding a plastic material of construction.

Plastic materials of construction also provide the self-locking arm (see reference characters 34, 134, and 234 in the drawings) with sufficient material compliance and elasticity to allow repeated elastic deformation—i.e., elastic movement of the self-locking arm inwardly and away from its biased position without plastic (permanent) deformation or material failure—for a sufficiently large number of cycles.

Although not shown in FIGS. 1A-4B and 7A-11C, the fluid line locking devices can further comprise a sealant attached to one or more of the closure surfaces and/or bearing surfaces. For example, the fluid line locking device 10 shown in FIGS. 1A-1F can comprise a sealant attached to the first closure surface 16a, the second closure surface 16b, the first proximal bearing surface 46a, the second proximal bearing surface 46b, the first distal bearing surface 48a, or the second distal bearing surface 48b, or any combination thereof. Similarly, the fluid line locking device 110 shown in FIGS. 8A and 8B can comprise a sealant attached to the first closure surface 116a, the second closure surface 116b, the engaging portions of the first and second extended hinge walls 118a and 118b, the first proximal bearing surface 146a, the second proximal bearing surface 146b, the first distal bearing surface 148a, or the second distal bearing surface 148b, or any combination thereof. Likewise, the fluid line locking device 210 shown in FIGS. 11A-11C can comprise a sealant attached to the first closure surface 216a, the second closure surface 216b, the first hinge closure surface 218a, the second hinge closure surface 218b, or any of the bearing surfaces, or any combination thereof.

The attached sealant may comprise, for example, a silicone layer deposited on the surfaces. Alternatively, the attached sealant may comprise, for example, a gasket structure such as an O-ring. The attachment of a sealant to closure surfaces and/or bearing surfaces may further prevent liquid from infiltrating into or out of the interior volume of the closed fluid line locking device, which may further decrease the likelihood of bacterial contamination and infection, for example, in medical applications where the fluid line locking device comprising the attached sealant is used to enclose and secure a Luer lock connection.

Figure 13:
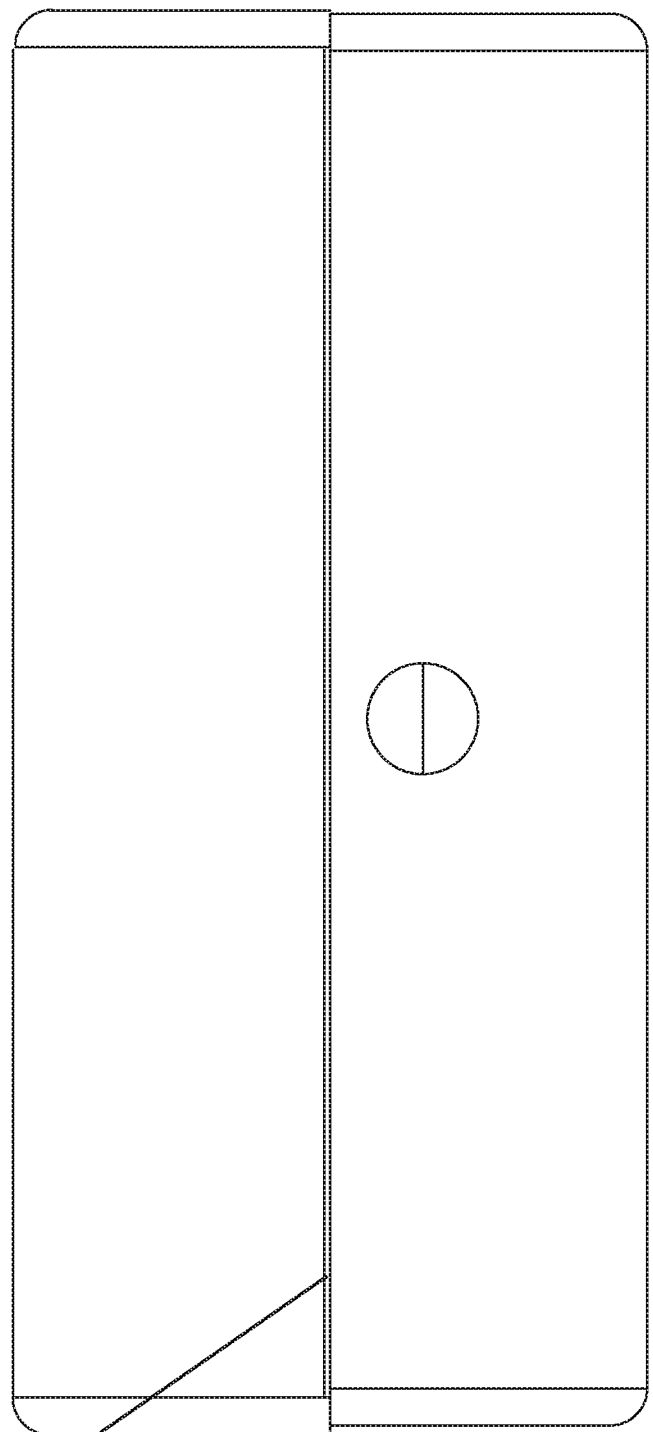
FIG. 13 is a photograph of the prototype fluid line locking device shown in FIG. 12 engaging and enclosing a standard Luer lock connection.

A prototype fluid line locking device was made in accordance with the embodiments described in this specification. The prototype is shown in FIGS. 12 and 13. The two enclosing components, the hinge, the lock components, and the bearing surfaces are shown in FIG. 12. A sealant 1000 comprising a deposited silicone layer is shown attached to the bearing surfaces. Referring to FIG. 13, the prototype fluid line locking device is shown enclosing and securing a standard Luer lock fluid connection.

As described above, the fluid line locking devices described in this specification may be particularly beneficial in medical applications, for example, to enclose and secure Luer lock connections between central lines or other catheters and IV source lines, particularly with pediatric patients. The fluid line locking devices can be easily applied and conveniently removed by clinicians or other medical staff, but the automatic snap fit self-locking mechanism prevents pediatric patients from tampering with the enclosed Luer lock connection and inadvertently disconnecting the IV source line, which decreases the likelihood of bacterial contamination entering into the catheter line and reduces the potential for infection.

Additionally, disinfectant caps are not currently used on disconnected catheter lines with pediatric patients, because of the choking hazard presented by the caps if a child patient unscrews the cap, which increases the potential for bacterial contamination and infection. However, the fluid line locking devices described in this specification will allow the use of disinfectant caps with pediatric patients, thus further decreasing the potential for contamination and infection, because the fluid line locking devices can enclose and secure the disinfectant caps onto standard female Luer lock fittings (and disinfectant tips onto standard male Luer lock fittings).

Although the fluid line locking devices are described in this specification in connection with standard Luer lock connections in medical applications, it is nevertheless understood that the fluid line locking devices may be used in other applications employing Luer lock connections, such as, for example, with laboratory equipment. Additionally, the fluid line locking devices described in this specification can be structured and dimensioned to enclose and secure fluid line connection joints other than standard Luer lock connections. For example, the fluid line locking devices may be used in lockout-tagout applications as part of an occupational health and safety compliance protocol.

Various features and characteristics of the inventions are described in this specification to provide an overall understanding of the disclosed fluid line locking device. It is understood that the various features and characteristics described in this specification can be combined in any suitable manner regardless of whether such features and characteristics are expressly described in combination in this specification. The Applicants/Inventors expressly intend such combinations of features and characteristics to be included within the scope of this specification. As such, the claims can be amended to recite, in any combination, any features and characteristics expressly or inherently described in, or otherwise expressly or inherently supported by, this specification. Furthermore, the Applicants/Inventors reserve the right to amend the claims to affirmatively disclaim features and characteristics that may be present in the prior art, even if those features and characteristics are not expressly described in this specification. Therefore, any such amendments will comply with the written description requirement of 35 U.S.C. § 112(a), and will not add new matter to the specification or claims. The fluid line locking device disclosed in this specification can comprise, consist of, or consist essentially of the various features and characteristics described in this specification.

Any patent, publication, or other disclosure material identified in this specification is incorporated by reference into this specification in its entirety unless otherwise indicated, but only to the extent that the incorporated material does not conflict with existing descriptions, definitions, statements, or other disclosure material expressly set forth in this specification. As such, and to the extent necessary, the express disclosure as set forth in this specification supersedes any conflicting material incorporated by reference. Any material, or portion thereof, that is incorporated by reference into this specification, but which conflicts with existing definitions, statements, or other disclosure material set forth herein, is only incorporated to the extent that no conflict arises between that incorporated material and the existing disclosure material. Applicant reserves the right to amend this specification to expressly recite any subject matter, or portion thereof, incorporated by reference.

The grammatical articles "one", "a", "an", and "the", as used in this specification, are intended to include "at least one" or "one or more", unless otherwise indicated. Thus, the articles are used in this specification to refer to one or more than one (i.e., to "at least one") of the grammatical objects of the article. By way of example, "a component" means one or more components, and thus, possibly, more than one component is contemplated and can be employed or used in an implementation of the described processes, compositions, and products. Further, the use of a singular noun includes the plural, and the use of a plural noun includes the singular, unless the context of the usage requires otherwise.

REFERENCE CHARACTERS USED IN THE DRAWINGS

| Reference characters | Components/features |
|---|---|
| 10 | fluid line locking device |
| 12a | first enclosing component |
| 12b | second enclosing component |
| 14a | first enclosing wall |
| 14b | second enclosing wall |
| 16a | first closure surface |
| 16b | second closure surface |
| 17 | closure joint |
| 20 | hinge |
| 21 | arrows (showing the rotational motion of the two enclosing components through the hinge) |
| 22a | first knuckles |
| 22b | second knuckles |
| 24 | pin |
| 30 | lock |
| 31 | arrows (showing the unlocking motion of the self-locking arm and the disengagement of the lock flanges) |
| 32a | first lock flange |
| 32b | second lock flange |
| 33a | first oblique guiding surface |
| 33b | second oblique guiding surface |
| 34 | self-locking arm |
| 36 | lock actuation aperture |
| 42a | first exterior surface |
| 42b | second exterior surface |
| 44a | first interior surface |
| 44b | second interior surface |
| 46a | first proximal bearing surface |
| 46b | second proximal bearing surface |
| 47 | proximal end aperture |
| 48a | first distal bearing surface |
| 48b | second distal bearing surface |
| 49 | distal end aperture |
| 50 | male Luer fitting |
| 52 | fluid conduit |
| 60 | female Luer fitting |
| 62 | fluid conduit |
| 70 | male Luer lock fitting |
| 72 | fluid conduit |
| 74 | fixed internally-threaded collar |
| 70' | male Luer lock fitting |
| 72' | fluid conduit |
| 74' | rotatable internally threaded collar |
| 80 | female Luer lock fitting |
| 82 | fluid conduit |
| 84 | thread lugs |
| 80' | female Luer lock fitting |
| 82' | fluid conduit |
| 84' | external threads |
| 90 | Luer lock connection |
| 92 | male Luer lock fitting |
| 94 | female Luer lock fitting |
| 96 | tubing |
| 98 | disinfectant cap |
| 110 | fluid line locking device |
| 112a | first enclosing component |
| 112b | second enclosing component |
| 114a | first enclosing wall |
| 114b | second enclosing wall |
| 116a | first closure surface |
| 116b | second closure surface |

-continued

| Reference characters | Components/features |
| --- | --- |
| 117 | closure joint |
| 118a | first hinge wall |
| 118b | second hinge wall |
| 119 | closure joint |
| 120 | hinge |
| 121 | arrows (showing the rotational motion of the two enclosing components through the hinge) |
| 122a | first knuckles |
| 122b | second knuckles |
| 124 | pin |
| 130 | lock |
| 131 | arrow (showing the unlocking motion of the self-locking arm and the disengagement of the lock flanges) |
| 132a | first lock flange |
| 132b | second lock flange |
| 133a | first oblique guiding surface |
| 133b | second oblique guiding surface |
| 134 | self-locking arm |
| 136 | lock actuation aperture |
| 142a | first exterior surface |
| 142b | second exterior surface |
| 144a | first interior surface |
| 144b | second interior surface |
| 146a | first proximal bearing surface |
| 146b | second proximal bearing surface |
| 147 | proximal end aperture |
| 148a | first distal bearing surface |
| 148b | second distal bearing surface |
| 149 | distal end aperture |
| 210 | fluid line locking device |
| 212a | first closing surface |
| 212b | second closing surface |
| 216a | first closure surface |
| 216b | second closure surface |
| 218a | first hinge closure surface |
| 218b | second hinge closure surface |
| 220 | living hinge |
| 221 | arrows (showing the rotational motion of the two enclosing components through the hinge) |
| 232a | first lock flange |
| 232b | second lock flange |
| 234 | self-locking arm |
| 236 | lock actuation aperture |
| 242a | first exterior surface |
| 242b | second exterior surface |

What is claimed is:

1. A fluid line locking device comprising:
a first enclosing component;
a second enclosing component connected to the first enclosing component through a hinge, wherein the first enclosing component and the second enclosing component are rotatable around the hinge from a closed configuration to an open configuration, wherein the hinge comprises a butt-mortise hinge comprising a pin located through a series of intermeshed knuckles, wherein a first set of the knuckles are integrally formed in the first enclosing component and mortised flush with the exterior surface of the first enclosing component, wherein a second set of the knuckles are integrally formed in the second enclosing component and mortised flush with an exterior surface of the second enclosing component, wherein the first enclosing component comprises an extended hinge wall separating the first set of knuckles from an interior volume of the fluid line locking device in the closed configuration, and wherein the second enclosing component comprises an extended hinge wall separating the second set of knuckles from the interior volume of the fluid line locking device in the closed configuration; and
a lock configured to secure the first enclosing component and the second enclosing component in the closed configuration, the lock comprising:
a first lock flange located on an interior surface of the first enclosing component;
a self-locking arm located on an interior surface of the second enclosing component;
a second lock flange located on the self-locking arm; and
a lock actuation aperture extending from an exterior surface of the first enclosing component and through the first lock flange.

2. The fluid line locking device of claim 1, wherein the lock further comprises:
a first oblique guiding surface located on the interior surface of the first enclosing component adjacent to the first lock flange; and
a second oblique guiding surface located on the self-locking arm adjacent to the second lock flange;
wherein engagement of the first oblique guiding surface and the second oblique guiding surface guides the second lock flange into engagement with the first lock flange during closing rotation of the first enclosing component and the second enclosing component around the hinge; and
wherein the self-locking arm is biased in a position where the second lock flange engages the first lock flange in the closed configuration.

3. The fluid line locking device of claim 1, wherein the first lock flange is integrally formed in the interior surface of the first enclosing component, wherein the self-locking arm is integrally formed with an interior surface of the second enclosing component, and wherein the second lock flange is integrally formed on the self-locking arm.

4. The fluid line locking device of claim 1, further comprising:
a first proximal bearing surface and a first distal bearing surface located at opposite longitudinal ends of the first enclosing component and separated by a first interior surface of the first enclosing component; and
a second proximal bearing surface and a second distal bearing surface located at opposite longitudinal ends of the second enclosing component and separated by a second interior surface of the second enclosing component;
wherein the first proximal bearing surface and the second proximal bearing surface collectively form a proximal end aperture in the fluid line locking device in the closed configuration;
wherein the first distal bearing surface and the second distal bearing surface collectively form a distal end aperture in the fluid line locking device in the closed configuration;
wherein the first proximal bearing surface and the second proximal bearing surface are structured and dimensioned to secure a standard male Luer lock fitting within an interior volume of the fluid line locking device in the closed configuration; and
wherein first distal bearing surface and the second distal bearing surface are structured and dimensioned to secure a standard female Luer lock fitting within the interior volume of the fluid line locking device in the closed configuration.

5. The fluid line locking device of claim 4, wherein the first proximal bearing surface, the second proximal bearing surface, the first distal bearing surface, or the second distal bearing surface, or any combination thereof, comprises an attached sealant comprising a deposited silicone layer attached to the surface or surfaces.

6. The fluid line locking device of claim 1, further comprising:
a first closure surface on the first enclosing component located adjacent to the first exterior surface; and
a second closure surface on the second enclosing component located adjacent to a second exterior surface;
wherein the first closure surface and the second closure surface approach and engage during the closing rotation of the first enclosing component and the second enclosing component around the hinge, thereby forming a closure joint in the closed configuration.

7. The fluid line locking device of claim 6, wherein the first closure surface and/or the second closure surface comprises an attached sealant comprising a deposited silicone layer attached to the surface or surfaces.

8. The fluid line locking device of claim 1, wherein the hinge closure surface on the first enclosing component and/or the hinge closure surface on the second enclosing component comprises an attached sealant comprising a deposited silicone layer attached to the surface or surfaces.

9. The fluid line locking device of claim 1, wherein the first enclosing component and the second enclosing component comprise a plastic material of construction.

10. The fluid line locking device of claim 9, wherein the plastic material of construction is transparent to visible light so that a user can view a fluid line connection joint enclosed and secured within the fluid line locking device in the closed configuration.

11. The fluid line locking device of claim 1, wherein the first enclosing component and the second enclosing component comprise hemi-cylindrical exterior surfaces and the fluid line locking device comprises a cylindrical shape in the closed configuration.

12. A fluid line locking device comprising:
a first hemi-cylindrical enclosing component;
a second hemi-cylindrical enclosing component connected to the first enclosing component through a living hinge, wherein the living hinge is integrally connected to the first enclosing component and the second enclosing component, and wherein the first enclosing component and the second enclosing component are rotatable around the living hinge from a closed configuration to an open configuration;
a lock configured to secure the first hemi-cylindrical enclosing component and the second hemi-cylindrical enclosing component in the closed configuration, the lock comprising:
a first lock flange integrally formed in an interior surface of the first hemi-cylindrical enclosing component;
a self-locking arm integrally formed on an interior surface of the second hemi-cylindrical enclosing component;
a second lock flange integrally formed on the self-locking arm; and
a lock actuation aperture extending from an exterior surface of the first hemi-cylindrical enclosing component and through the first lock flange;
a first proximal bearing surface and a first distal bearing surface located at opposite longitudinal ends of the first hemi-cylindrical enclosing component and separated by a first interior surface of the first hemi-cylindrical enclosing component; and
a second proximal bearing surface and a second distal bearing surface located at opposite longitudinal ends of the second hemi-cylindrical enclosing component and separated by a second interior surface of the second hemi-cylindrical enclosing component;
wherein the first proximal bearing surface and the second proximal bearing surface collectively form a proximal end aperture in the fluid line locking device in the closed configuration;
wherein the proximal end aperture comprises a first diameter;
wherein the first distal bearing surface and the second distal bearing surface collectively form a distal end aperture in the fluid line locking device in the closed configuration;
wherein the distal end aperture comprises a second diameter;
wherein the first interior surface of the first hemi-cylindrical enclosing component and the second interior surface of the second hemi-cylindrical enclosing component collectively form an interior aperture in the fluid line locking device in the closed configuration;
wherein the interior aperture comprises a third diameter;
wherein the first diameter is larger than the second diameter;
wherein the third diameter is larger than the first diameter;
wherein the first proximal bearing surface and the second proximal bearing surface are structured and dimensioned to secure a standard male Luer lock fitting within an interior volume of the fluid line locking device in the closed configuration;
wherein first distal bearing surface and the second distal bearing surface are structured and dimensioned to secure a standard female Luer lock fitting within the interior volume of the fluid line locking device in the closed configuration; and
wherein the first proximal bearing surface, the second proximal bearing surface, the first distal bearing surface, or the second distal bearing surface, or any combination thereof, comprises an attached sealant comprising a deposited silicone layer attached to the surface or surfaces.

13. The fluid line locking device of claim 12, wherein the lock further comprises:
a first oblique guiding surface located on the interior surface of the first hemi-cylindrical enclosing component adjacent to the first lock flange; and
a second oblique guiding surface located on the self-locking arm adjacent to the second lock flange;
wherein engagement of the first oblique guiding surface and the second oblique guiding surface guides the second lock flange into engagement with the first lock flange during closing rotation of the first hemi-cylindrical enclosing component and the second hemi-cylindrical enclosing component around the living hinge; and
wherein the self-locking arm is biased in a position where the second lock flange engages the first lock flange in the closed configuration.

14. The fluid line locking device of claim 12, wherein the living hinge is integrally connected to the first hemi-cylindrical enclosing component at an intersection of the exterior surface of the first hemi-cylindrical enclosing component and a hinge closure surface located on the first hemi-cylindrical enclosing component adjacent to the exterior surface, and wherein the living hinge is integrally connected to the second hemi-cylindrical enclosing component at an intersection of an exterior surface of the second hemi-cylindrical enclosing component and a hinge closure surface located on the second hemi-cylindrical enclosing component adjacent to the exterior surface.

15. The fluid line locking device of claim 12, further comprising:
a first closure surface on the first hemi-cylindrical enclosing component located adjacent to the first exterior surface; and
a second closure surface on the second hemi-cylindrical enclosing component located adjacent to the second exterior surface;
wherein the first closure surface and the second closure surface approach and engage during the closing rotation of the first hemi-cylindrical enclosing component and the second hemi-cylindrical enclosing component around the hinge, thereby forming a closure joint in the closed configuration.

16. The fluid line locking device of claim 12, wherein the first enclosing component and the second enclosing component comprise a plastic material of construction.

17. The fluid line locking device of claim 16, wherein the plastic material of construction is transparent to visible light so that a user can view a fluid line connection joint enclosed and secured within the fluid line locking device in the closed configuration.

18. A fluid line locking device, comprising:
a first enclosing component;
a second enclosing component connected to the first enclosing component through a hinge, wherein the first enclosing component and the second enclosing component are rotatable around the hinge from a closed configuration to an open configuration, wherein the first enclosing component comprises an extended hinge wall, wherein the second enclosing component comprises an extended hinge wall, and wherein the extended hinge walls cooperate to separate the hinge from the interior volume of the fluid line locking device in the closed configuration;
a lock configured to secure the first enclosing component and the second enclosing component in the closed configuration, the lock comprising:
a first lock flange located on an interior surface of the first enclosing component;
a self-locking arm located on an interior surface of the second enclosing component;
a second lock flange located on the self-locking arm; and
a lock actuation aperture extending from an exterior surface of the first enclosing component and through the first lock flange;
a first proximal bearing surface and a first distal bearing surface located at opposite longitudinal ends of the first enclosing element and separated by a first interior surface; and
a second proximal bearing surface and a second distal bearing surface located at opposite longitudinal ends of the second enclosing element and separated by a second interior surface, wherein the first proximal bearing surface, the second proximal bearing surface, the first distal bearing surface, or the second distal bearing surface, or any combination thereof, comprises an attached sealant comprising a deposited silicone layer attached to the surface or surfaces.

19. The fluid line locking device of claim 18, wherein the hinge comprises a living hinge integrally connected to the first enclosing component and the second enclosing component, wherein the living hinge is integrally connected to the first enclosing component at an intersection of the exterior surface of the first enclosing component and a hinge closure surface located on the first enclosing component adjacent to the exterior surface, and wherein the living hinge is integrally connected to the second enclosing component at an intersection of an exterior surface of the second enclosing component and a hinge closure surface located on the second enclosing component adjacent to the exterior surface.

* * * * *